US006635434B1

(12) United States Patent
Jakobsen et al.

(10) Patent No.: US 6,635,434 B1
(45) Date of Patent: Oct. 21, 2003

(54) IMMUNOASSAY FOR PESTICIDES AND THEIR DEGRADATION PRODUCTS

(75) Inventors: Mogens Havsteen Jakobsen, Vanløse (DK); Leif Bruun, Tåstrup (DK); Brian Pedersen, Søborg (DE)

(73) Assignee: Exiqon A/S, Vedbaek (DK)

( * ) Notice: Subject to any disclaimer, the term of this patent is extended or adjusted under 35 U.S.C. 154(b) by 31 days.

(21) Appl. No.: 09/621,025

(22) Filed: Jul. 21, 2000

Related U.S. Application Data

(60) Provisional application No. 60/154,596, filed on Sep. 17, 1999.

(51) Int. Cl.[7] ............... G01N 33/533; G01N 33/535; G01N 33/545; G01N 33/552; C07K 17/02; C07K 16/44

(52) U.S. Cl. ............... 435/7.93; 435/7.94; 436/527; 436/531; 436/546; 436/815; 530/404; 530/405; 530/389.5

(58) Field of Search ............... 435/7.93, 7.94; 530/389.8, 404, 405; 436/815, 527, 531, 546

(56) References Cited

U.S. PATENT DOCUMENTS

| 5,100,776 A | 3/1992 | Pfeiffer et al. |
| 5,654,178 A | 8/1997 | Fitzpatrick et al. |
| 5,674,697 A | 10/1997 | Carlson |
| 5,723,306 A | 3/1998 | Pullen et al. |
| 5,830,770 A | 11/1998 | Matthews et al. |

FOREIGN PATENT DOCUMENTS

| CH | 0365 818 | 9/1989 |
| EP | 0330517 B2 | 8/1989 |
| EP | 0638805 A2 | 10/2001 |
| JP | 60/24199 | 2/1985 |
| WO | 0201 633 | 12/1985 |
| WO | WO 91/05259 | 4/1991 |
| WO | WO 92/12427 | 7/1992 |
| WO | WO 94/01544 | 1/1994 |
| WO | WO 94/01578 | 1/1994 |

OTHER PUBLICATIONS

Database Medline (Online) US National Library of Medicine (NLM), Bethesda, MD, US: Fleeker, J. retrieved from Medline, accession No. 88058682 XP002901439 abstract & J Assoc Off Anal Chem. vol. 70, No. 5, Sep. 1987—Oct. 1987, pp. 874–878.

Database Dialog Info Serv (Online) File 34, SciSearch Dialog; Brunn L et al retrieved from Dialog Information Services, accession No. 08758396 XP002901440 abstract & J of Immunological Methods, vol. 240, No. 1–2, Jun. 23, 2000, pp. 133–142 ISSN. 0022–1759.

Primary Examiner—Mary E. Ceperley
(74) Attorney, Agent, or Firm—Peter F. Corless; Dianne M. Rees; Edwards & Angell, LLP

(57) ABSTRACT

A hapten-polymer carrier complex was found to be useful for immunoassay purposes, specifically ELISAs, for the detection of pesticides and their degradation products in hydrosoil and ground water. The degradation products of Casoron G® (also known as dichlorobenzonitrile and dichlorbenil) and Prefix® (also known as chlorthiamid and dichlorobenzthiamide) are analytes detected with high specificity and sensitivity, particularly the degradation product BAM (2,6-dichlorobenzamide). The polymer carrier complex is bound to the hapten via a linker unit, strategically positioned meta to the amide or amide derivative of BAM.

62 Claims, 8 Drawing Sheets

Figure 1:
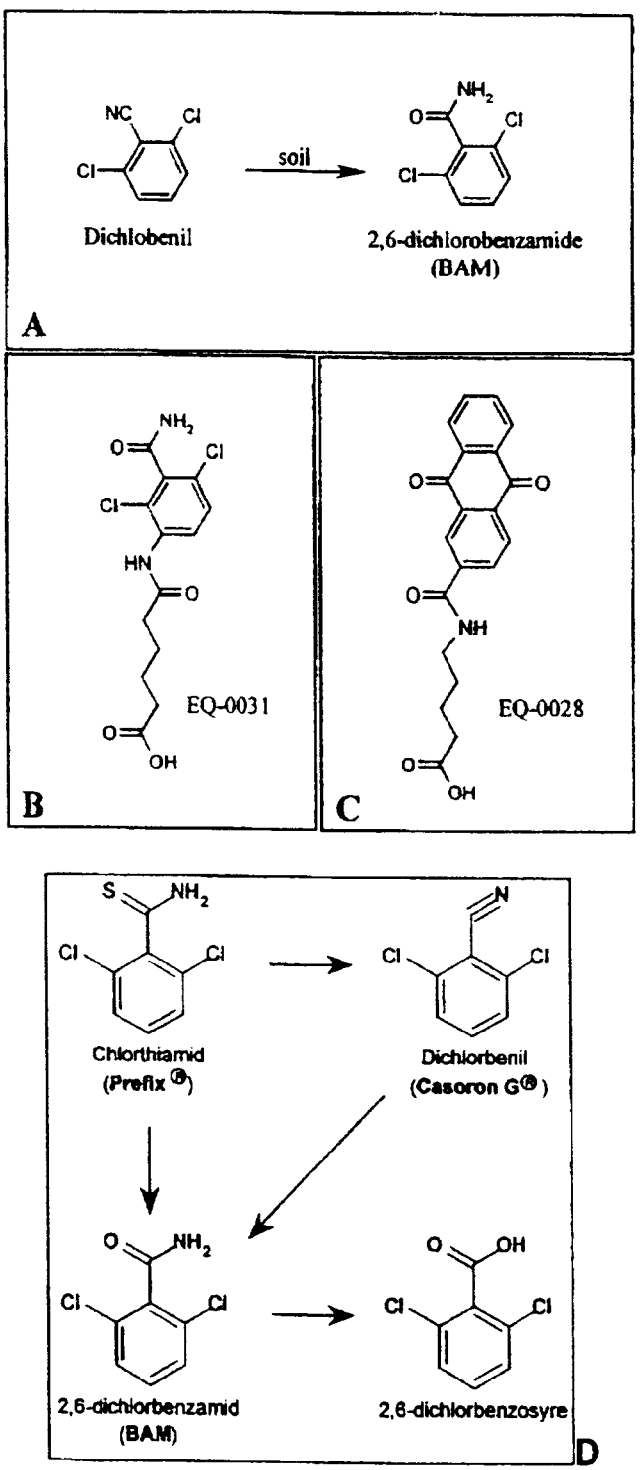

|  | Ballerup | Vejen | Milli Q |
|---|---|---|---|
| pH: | 7.8 | 6.3 | 7.0 |
| DOC (mg/L): | 6.2 | 8.6 | < 0.1 |
| Ions (mg/L) | | | |
| $Na^+$ | 27.3 | 9.7 | 0.07 |
| $K^+$ | 1.7 | 3.1 | < 0.10 |
| $Ca^{++}$ | 113.0 | 23.0 | 0.025 |
| $Mg^{++}$ | 5.1 | 2.3 | 0.03 |
| $Fe^{++}$ | 0.06 | 0.02 | < 0.02 |
| Mn | 0.21 | 0.02 | < 0.01 |
| $Cl^-$ | 21.4 | 17.7 | < 0.02 |
| $NO_3^-$ | 0.67 | 29.2 | < 0.02 |
| $SO_4^-$ | 54.6 | 29.0 | < 0.02 |

DOC: Dissolved Organic Carbon

Fig. 6

| Sample | Assay | Spike (µg/L) | | | | |
|---|---|---|---|---|---|---|
| | | 0 | 0.05 | 0.1 | 0.5 | 1 |
| Vejen | 1 | 0.010 | 0.058 | 0.108 | 0.511 | 0.970 |
| | 2 | 0.010 | 0.058 | 0.104 | 0.570 | 1.086 |
| | 3 | 0.010 | 0.053 | 0.103 | 0.493 | 1.054 |
| | 4 | 0.020 | 0.057 | 0.092 | 0.533 | 1.026 |
| | mean | 0.013 | 0.057 | 0.102 | 0.527 | 1.034 |
| | CV % | 34.6 | 3.6 | 5.8 | 5.5 | 4.1 |
| | recovery | | 113.0 | 101.8 | 105.4 | 103.4 |
| Ballerup | 1 | 0.011 | 0.054 | 0.100 | 0.565 | 1.012 |
| | 2 | 0.015 | 0.054 | 0.106 | 0.549 | 1.019 |
| | 3 | 0.021 | 0.054 | 0.104 | 0.525 | 0.969 |
| | 4 | 0.013 | 0.053 | 0.096 | 0.523 | 1.006 |
| | mean | 0.015 | 0.054 | 0.102 | 0.541 | 1.002 |
| | CV % | 24.9 | 0.8 | 3.8 | 3.2 | 1.9 |
| | recovery | | 107.5 | 101.5 | 108.1 | 100.2 |
| milliQ | 1 | 0.011 | 0.048 | 0.113 | 0.505 | 0.949 |
| | 2 | 0.010 | 0.049 | 0.095 | 0.552 | 1.023 |
| | 3 | 0.010 | 0.055 | 0.105 | 0.493 | 1.012 |
| | 4 | 0.011 | 0.046 | 0.100 | 0.552 | 1.077 |
| | mean | 0.011 | 0.050 | 0.103 | 0.526 | 1.015 |
| | CV % | 4.8 | 6.8 | 6.4 | 5.1 | 4.5 |
| | recovery | | 99.0 | 103.3 | 105.1 | 101.5 |

Fig. 7

| Analyte | Structure | IC$_{50}$ (μg/L) | Cross-reactivity (%) |
|---|---|---|---|
| 2,6-dichlorobenzamide (BAM) | 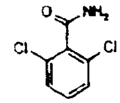 | 0.2 | 100 |
| 2,4-dichlorobenzamide | 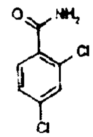 | 5.3 | 3.8 |
| o-chlorobenzamide | 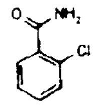 | 13.0 | 1.5 |
| p-chlorobenzamide | 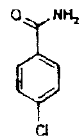 | 900 | 0.02 |
| 2,6-Dichloro-benzenemethanol | 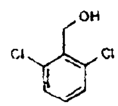 | 4000 | 0.005 |
| 2,6-dichlorobenzonitrile (Dichlobenil) | 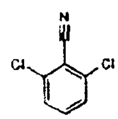 | 5000 | 0.004 |
| 2,6-Dichlorobenzoic Acid | 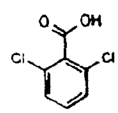 | 50,000 | 0.0004 |
| 2,5-dichloro-3-aminobenzoic acid (Amiben) | 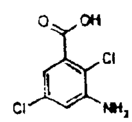 | > 100,000 | < 0.0002 |
| Propyzamide (Kerb) | 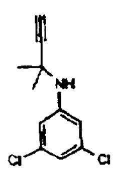 | > 100,000 | < 0.0002 |

Fig. 8

IMMUNOASSAY FOR PESTICIDES AND THEIR DEGRADATION PRODUCTS

The present applications claims the benefit of U.S. provisional application No. 60/154,596, filed Sep. 17, 1999, and which is incorporated by reference herein in its entirety.

FIELD OF INVENTION

The present invention relates to a novel hapten-polymer carrier complex comprising a linking unit located so as to not disrupt the antigenic determinant groups of the hapten. The invention further relates to a specific immunoassay for the identification and quantification of pesticides and their degradation products using said hapten.

GENERAL BACKGROUND

Pesticides are widely used in many countries. Dichlorbenil (Casoron G®, dichlorobenzonitrile) is a pesticide used as a broad-spectrum herbicide both in agriculture and in urban areas. This herbicide is degraded, mainly to 2,6-dichlorobenzamide (BAM) by biotic or abiotic processes in the hydrosoil (FIG. 1A) (Beynon and Wright, 1972; Montgomery et al., 1972; Verloop, 1972). Chlorthiamid (Prefix®), a commercial pesticide, also degrades to BAM (FIG. 1D). BAM is very persistent, and is now contaminating a large number of ground-water areas in Europe and the U.S.A.(Brüsch, 1998). To prevent further leaching of BAM to the drinking water, dichlorbenil is now banned in many countries.

Most BAM-analyses are based on high-performance liquid chromatography (HPLC) and gas chromatography (GC) (van Rossum et al., 1978; Connick and Bradow, 1984) which have detection limits of approximately 0.01 µg/L. Such analyses are very costly for national groundwater-monitoring programs. To lower expenses on pesticide analyses, immunoassays have been developed for several pesticides (Kaufman and Clower, 1995; Issert et al., 1997), but not yet for BAM or the degradation products of dichlorbenil.

The advantage of immunoassays is their extremely high sensitivity, which enables the quantification of pesticides or their degradation products in concentrations lower than 1 µg/L without the need for concentration of samples. Analyses based on HPLC and GC (and GC mass spectroscopy, GC-MS) often require concentration of the sample by evaporation of approximately 2 L of aqueous sample to volumes one thousandth of the original volume.

An immunoassay involves the detection or measurement of an analyte using the specific interaction between an antibody and an antigen. The immune complex that occurs specifically between the antigen and the antibody forms the foundation of such assays. Usually, the antibody is labelled with a tag for detection or quantification purposes. An assay comprising of an enzyme-linked antibody (or antigen) complexing to an immobolised antigen (or antibody) is commonly referred to as an ELISA (enzyme-linked immunosorbent assay).

An immunological process for the assaying a class of herbicides have previously been described (EP 0 300 381 B1). However, this class of compounds does not foresee the use of an appropriate linking unit moiety, nor does it anticipate the class of compounds or haptens described herein. It describes an immunological process for the assay of tri-substituted aromatic rings in which two of the three substituents are fixed 1,3 with respect to one another (meta to one another) whereas the third substituent can be in positions 2, 4, 5, or 6 (ortho or para to either of the other two substituents). Moreover, any of the three substituents can serve to couple to a solid matrix. The hapten, which is the same as the hapten immobilised to the matrix, was used to raise antibodies A, B, or C for the purpose of the assay and that at least two of the said antibodies were reacted separately with a sample supposedly containing said hapten.

Hammock et al (*J. Agric. Food Chem.* 1984, 32, 1294) investigated the sensitivity and specificity of immunoassays for benzoylphenylureas in relation to heterologous site systems and homologous site systems whereby the coupling site of the hapten was varied or remained constant, respectively.

In U.S. Pat. No. 5,654,178, an antibody useful in an immunoassay for tetrachloroisophthalonitrile is raised. The hapten is coupled to protein via a functional group interchange of a chloro group present on the ring.

SUMMARY OF THE INVENTION

A first aspect of the invention relates to a hapten-polymer carrier complex comprising a polymer carrier and a compound of the general formula I

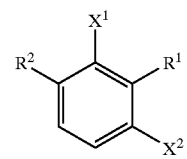

I wherein $R^2$ serves as a linking unit to the polymeric carrier to form the hapten-polymer carrier complex; and wherein $R^1$ is selected from the group consisting of —C(=O)—N($R^5$)($R^5$, —N($R^5$)—C(=O)—O$R^5$, —C(=O)—O$R^5$, —N($R^5$)—C(=O)($R^5$, —N($R^5$)—C(=S)($R^5$, —C(=S)—n($R^5$)($R^5$, —N($R^5$)—C(=S)—N($R^5$)($R^5$, —N($R^5$)—C(=O)—N($R^5$)($R^5$, —O—C(=O)—$R^5$, —C(=S)—O$R^5$, —o—C(=S)—$R^5$, —O—$R^5$, —N($R^5$)($R^5$, —S—$R^5$, —CH$_2$—$R^5$, —NC, and halogen; where $R^5$ is independently selected from the group consisting of hydrogen, optionally substituted $C_{1-4}$ alkyl, optionally substituted $C_{1-6}$ alkenyl, optionally substituted $C_{2-6}$ alkynyl, optionally substituted aryl, optionally substituted heteroaryl, and optionally substituted $C_3$–$C_7$ cycloalkyl; and wherein $X^1$ and $X^2$ are independently selected from halogens.

In a second aspect, the invention relates to a use of said complex for the identification or quantification of a pesticide and/or its degradation product or products by an immunoassay involving antibodies raised from said hapten-polymer carrier complex.

A second aspect of the invention relates to a method, for the identification or quantification of a pesticide and/or its degradation product or products by an immunoassay involving antibodies raised from a hapten-polymer carrier complex of general formula I,

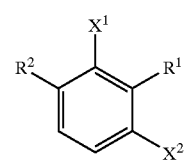

I wherein $X^1$, $X^2$, $R^1$, $R^2$ are as defined as above; and
  a compound of the general formula II immobilised to a solid support

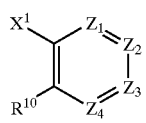

II wherein $Z_1$ is C—$R^6$, $Z_2$ is C—$R^7$, $Z_3$ is C—$R^8$ and $Z_4$ is C—$R^8$, where at least one of $R^6$–$R^{10}$ is present and serves as a linking unit for immobilisation of the hapten to the solid support, and the ones of $R^6$–$R^{10}$ which are present and which do not serve as a linking unit are independently selected from the group consisting of —C(=O)—$NH_2$, —N($R^5$)($R^5$), —CN, N($R^5$)—C(=O)($R^5$), —N($R^5$)—C(=S)($R^5$), —C(=S)—N($R^5$)($R^5$, —N($R^5$)—C(=S)—N($R^5$)($R^5$), —N($R^5$)—C(=O)—N($R^5$)($R^5$), —N($R^5$)—C(=O)—$OR^5$, —C(=O)N($R^5$)($R^5$), —C(=O)—$OR^5$, —O—C(=O)—$R^5$, —C(=S)—$OR^5$, —O—C(=S)—$R^5$, hydrogen, and halogen; and wherein those of $R^6$–$R^{10}$ which serve as a linking unit are selected from the group consisting of —C(=O)—N($R^5$)—$(CH_2)_n$—$R^3$—$(CH_2)_m$—$R^4$, —N($R^5$)—C(=O)—$CH_2)_n$—$R^3$—$(CH_2)_m$—$R^4$, —O—$(CH_2)_n$—$R^3$—$(CH_2)_m$—$R^4$, —N($R^5$)—$(CH_2)_n$—$R^3$—$(CH_2)_m$—$R^4$, —S—$(CH_2)_n$—$R^3$—$(CH_2)_m$—$R^4$, —$(CH_2)_{n+1}$—$R^3$—$(CH_2)_m$—$R^4$, —C(=O)—O—$(CH_2)_n$—$R^3$—$(CH_2)_m$—$R^4$, and —O—C(=O)—$(CH_2)_n$—$R^3$—$(CH_2)_m$—$R^4$; wherein n and m are independent and are integers from 0 to 8; $R^3$ is selected from the group consisting of —O—C(=O)—, —C(=O)—O—, —O—C(=S)—, —O(—S)—O—, —N($R^5$)—C(=O)—, —C(=O)—N($R^5$)—, —O—, —S—, —N($R^5$)—, optionally substituted $C_{1-4}$ alkylene, optionally substituted arylene, optionally substituted heteroarylene, an optionally substituted $C_3$–$C_7$ cycloalkylene, $R^4$ is selected from the group consisting of activated forms of a carboxyl, carboxylic acid, amine, acyl halides, activated esters, thiols, disulphides (—S—S—R), halides, sulphonates, quinones and imides; and $R^5$ is independently selected from the group consisting of hydrogen, optionally substituted $C_{1-4}$ alkyl, optionally substituted $C_{2-5}$ alkenyl, optionally substituted $C_{2-6}$ alkynyl, optionally substituted aryl, optionally substituted heteroaryl, and optionally substituted $C_3$–$C_7$ cycloalkyl.

A third aspect of the invention relates to kit for an immunoassay comprising a solid support and hapten-polymeric carrier complex as defined above immobilised to said solid support.

DETAILED DESCRIPTION OF THE INVENTION

The present investigators have surprisingly found that in immunoassays for certain 1,3-dihalo aromatic pesticides, such as dichlorbenil, chlorthiamid and their derivatives and degradation products, linking of said hapten to a polymeric carrier via the 4-position provides for assays with excellent specificity and little cross-reactivity over hapten polymeric carrier complexes whereby the linking moiety is via the functional group at the 2-position or via either of the halo groups native to the pesticide. Furthermore, the location of the linker moiety at the non-activated 4 position provides improved specificity in immunoassays over hapten-polymeric carriers whereby the coupling of the hapten to a polymeric carrier is through an alternative non-activated position.

Specifically, positioning the linker moiety meta to the functional group at the 2 position of a 1,2,3-trisubstituted aromatic hapten, such as 2,6-dichlorbenzamide, for coupling to a polymeric carrier to form a hapten-polymeric carrier complex provides an excellent antigen for raising antibodies which are useful in immunoassays against dichlorbenil and chlorthiamid and their degradation products and derivatives.

The hapten-polymeric carrier complex allows for an immunoassay involving the use of antibodies raised from these novel complexes which are antigenic in animal systems. The raising of antibodies is performed prior to the immunoassay by any number of methods known by persons skilled in the art.

In the present context, the term "hapten" is intended to mean a compound which can combine with an antibody, but cannot initiate an immune response unless it is bound to a polymer carrier forming a hapten-polymer carrier complex, said complex serving as an antigen that elicits a specific immune response when introduced into the tissues of an animal. The term "hapten" is also intended to mean a compound that upon linking to a polymer carrier to for a hapten-polymer carrier complex, said complex serves as an antigen to an antibody in an immunoassay.

In the present context the term "$C_{1-4}$-alkylene" used alone or as part of another group designates a linear, branched or saturated diradical hydrocarbon group having from one to four carbon atoms, such as methyl, ethyl, n-propyl, isopropyl, n-butyl, isobutyl, sec-butyl, tert-butyl.

In the present context the term "$C_{1-4}$-alkyl" used alone or as part of another group designates a linear, branched or saturated monoradical hydrocarbon group having from one to four carbon atoms, such as methyl, ethyl, n-propyl, isopropyl, n-butyl, isobutyl, sec-butyl, tert-butyl.

In the present context the term "$C_{2-5}$-alkylene" is intended to mean a linear, branched or diradical having from two to five carbon atoms and containing one or more double bonds. Examples of $C_{2-8}$-alkenyl groups include olefins such as allyl, homo-allyl, vinyl, crotyl. butenyl, pentenyl. Examples of $C_{2-5}$-alkenyl groups with more than one double bond include butadienyl, pentadienyl as well as branched forms of these. Preferred examples of $C_{2-8}$-aklenyls are vinyl, allyl and butenyl.

In the present context the term "$C_{2-6}$-alkynyl" is intended to mean a linear, branched or monoradical having from two to five carbon atoms and containing one or more double bonds. Examples of $C_{2-6}$-alkenyl groups include olefins such as allyl, homo-allyl, vinyl, crotyl, butenyl, pentenyl. Examples of $C_{2-6}$-alkenyl groups with more than one double bond include butadienyl, pentadienyl as well as branched forms of these. Preferred examples of $C_{2-8}$-alkenyl are vinyl, allyl and butenyl.

In the present context the term "$C_{2-8}$-alkynylene" is intended to mean linear, branched diradical containing from two to five carbon atoms and containing one or more triple bonds. Examples of $C_{2-8}$-alkynyl groups include acetylene, propynyl, butynyl, pentynyl, hexynyl as well as branched forms of these.

In the present context the term "$C_{2-8}$-alkynyl" is intended to mean linear, branched monoradical containing from two to five carbon atoms and containing one or more triple bonds. Examples of $C_{2-8}$-alkynyl groups include acetylene, propynyl, butynyl, pentynyl, hexynyl as well as branched forms of these.

In the present context the term "arylene" used alone or as part of another group is intended to mean a biradical aromatic carbocyclic ring or ring system, such as phenyl, naphthyl, anthracyl, phenanthracyl, pyrenyl, benzopyrenyl, fluorenyl, and xanthenyl, preferably phenyl.

In the present context the term "aryl" used alone or as part of another group is intended to mean a monoradical aromatic carbocyclic ring or ring system, such as phenyl, naphthyl, anthracyl, phenanthracyl, pyrenyl, benzopyrenyl, fluorenyl, and xanthenyl, preferably phenyl.

The term "heteroarylene" is intended to mean an arylene group where one or more carbon atoms have been replaced with heteroatoms such as nitrogen, sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrazinyl, pyridazinyl, piperidinyl, coumaryl, furyl, quinolyl, indolyl, benzopyrazolyl, and phenoxazonyl.

The term "heteroaryl" is intended to mean an aryl group where one or more carbon atoms have been replaced with heteroatoms such as nitrogen, sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrazinyl, pyridazinyl, piperidinyl, coumaryl, furyl, quinolyl, indolyl, benzopyrazolyl, and phenoxazonyl.

In the present context the term "$C_3$–$C_7$ cycloalkylene" is intended to cover biradical three-, four-, five-, six- and seven-membered rings comprising carbon atoms only (carbocyclic) or carbon atoms together with from 1 to 3 heteroatoms (heterocyclic), wherein the heteroatoms are independently selected from oxygen, sulphur, and nitrogen. Such rings may contain no unsaturated bonds or may contain one or more unsaturated bonds, however, if present, situated in such a way that an aromatic π-electron system does not arise.

In the present context the term "$C_3$–$C_7$ cycloalkyl" is intended to cover monoradical three-, four-, five-, six- and seven-membered rings comprising carbon atoms only (carbocyclic) or carbon atoms together with from 1 to 3 heteroatoms (heterocyclic), wherein the heteroatoms are independently selected from oxygen, sulphur, and nitrogen. Such rings may contain no unsaturated bonds or may contain one or more unsaturated bonds, however, if present, situated in such a way that an aromatic π-electron system does not arise.

The term "halogen" includes fluorine, chlorine, bromine and iodine.

In the present context, i.e. in connection with the terms "arylene" and "heteroarylene", the term "optionally substituted" is intended to mean that the group in question may be substituted one or several times, such as 1 to 5 times, preferably 1 to 3 times, with one or more groups selected from $C_{1-4}$-alkyl, $C_{1-4}$-alkoxy, oxo (which may be represented in the tautomeric enol form), carboxy, amino, hydroxy (which when present in an enol system may be represented in the tautomeric keto form), nitro, sulphono, sulphanyl, $C_{1-4}$-carboxy, $C_{1-4}$-alkoxycarbonyl, $C_{1-4}$-alkylcarbonyl, formyl, aryl, arloxy, arloxycarbonyl, arylcarbonyl, heteroaryl, amino, mono- and di($C_{1-4}$-alkyl)amino; carbamoyl, mono- and di($C_{1-4}$-alkyl)-aminocarbonyl, amino-$C_{1-4}$-alkyl-aminocarbonyl, mono- and di($C_{1-4}$-alkyl)amino-$C_{1-4}$-alkyl-aminocarbonyl, $C_{1-4}$-alkylcarbonylamino, cyano, guanidino, carbamido, $C_{1-4}$-alkanoyloxy, sulphono, $C_{1-4}$-alkylsulphonyloxy, nitro, sulphanyl, dihalogen-$C_{1-4}$-alkyl, trihalogen-$C_{1-4}$-alkyl, halogen, where aryl and heteroaryl representing substituents may be substituted 1–3 times with $C_{1-4}$-alkyl, $C_{1-4}$-alkoxy, nitro, cyano, hydroxy, amino or halogen.

In the present context, the term "optionally substituted" in connection with "$C_{1-4}$-alkenylene", "$C_{2-5}$-alkenylene", "$C_{2-4}$-alkynylene", "$C_3$–$C_7$ cycloalkylene", "alkyl", "$C_{1-4}$-alkyl", "$C_{2-5}$-alkenyl", and "$C_{2-8}$-alkynyl is intended to mean that the group in question may be substituted one or more times with hydroxy; $C_{1-4}$-alkoxy optionally substituted one or more times with halogen, hydroxy, amino, mono- or di($C_{1-4}$-alkyl)amino, cyano, and carboxy; halogen; nitro; nitroso; cyano; carboxy; thiolo; $C_{1-4}$-alkylthio; aryloxyl, heteroaryloxy, arylthio; $C_{1-4}$-alkylsulphonyl; arylsulphonyl; sulphono ($SO_3H$); sulphino ($SO_2H$); halosulphonyl; isocyano; isothiocyano; and thiocyano.

I. The Compound Used for Immunisation a) The Linking Unit Moiety i) The coupling process As will be understood from examples herein, the position, length and nature of the linking unit of the haptens are of utmost importance for an immunoassay selective for degradation products and derivatives of dichlorbenil and chlorthiamid. The linking unit, optionally upon activation, serves to conjugate a polymer carrier to a hapten for the purpose of the immunisation of the animals. The linking unit may serve to orient the hapten for recognition by the antibody. The linking unit, $R^2$, in formula I, must be of appropriate length and flexibility to orient the hapten relative to the polymer carrier appropriately.

The linking unit, $R^2$, can comprise, at its terminus, of a functional group suitable for coupling to a polymer carrier or of a group suitable for activation. The terminus of the linking unit is either suitable for activation or is an activated species itself (termed a "pre-activated system") suitable for forming a covalent bond to a polymer carrier.

The person skilled in the art will be aware of a whole array of functional groups responsive to stimuli in photochemical, electrochemical, and chemical processes. Examples of functional groups considered to be photo-, thermo, electrochemical- or chemoreactive suitable for forming a covalent bond to the polymer carrier include, to name but a few, carboxylates, carboxylic acids, acyl halides, activated esters, thiols, disulphides (—S—S—R), amines, halides, sulphonates, quinones, diazotized amines, and imides.

In one embodiment of the invention, $R^2$ is selected from the group consisting of —C(=O)—N($R^5$)—$(CH_2)_n$—$R^3$—$(CH_2)_m$—$R^4$, —N($R^5$)—C(=O)—$(CH_2)_n$—$R^3$—$(CH_2)_m$—$R^4$, —O—$(CH_2)_n$—$R^3$—$(CH_2)_m$—$R^4$, —N($R^5$)—$(CH_2)_n$—$R^3$—$(CH_2)_m$—$R^4$, —S—$(CH_2)_n$—$R^3$—$(CH_2)_m$—$R^4$, —$(CH_2)_{m+1}$—$R^3$—$(CH_2)_m$—$R^4$, —O—C(=O)—$(CH_2)_n$—$R^3$—$(CH_2)_m$—$R^4$, and —C(=O)—O—$(CH_2)_m$—$R^3$—$(CH_2)_m$—$R^4$ wherein n and m independently are integers from 0 to 8; where $R^3$ is selected from the group consisting of —O—C(=O)—, —C(=O)—O—, —O—C(=S)—, —C(=S)—O—, —N($R^5$)—C(=O)—, —C(=O)—N($R^5$)—, —O—, —S—, —N($R^5$)—, optionally substituted $C_{1-4}$ alkylene, optionally substituted arylene, optionally substituted heteroarylene, and optionally substituted $C_3$–$C_7$ cycloalkylene.

In such embodiments, $R^4$ is the terminus of the linking unit and is a functional group suitable for chemo-, photo-, electro- or thermo-reactivity and combinations thereof. $R^4$ as such, can be selected from the group comprising of activated forms of a carboxylates, carboxylic acid, amine, acyl halides, activated esters, thiols, disulphides (—S—S—R), halides, sulphonates, quinones and imides. However, as is known by the person skilled in the art, the covalent linking of two components can be accomplished by countless methods too numerous to describe or enumerate (see Hermanson, Mallia and Smith, *Immobilized Affinity Ligand Techniques*, Academic Press, 1992, San Diego, Calif., USA).

The coupling of a hapten to a polymer carrier can proceed via a multitude of methods, as is known by the person skilled in the art. The method will of course be dependent on the functional groups present on the polymer carrier. Thus, the nature of $R^4$, and the nature of the terminus of $R^2$ in general will depend on the desired coupling technique and on the choice of polymer carrier, and consequently on the functional groups present on the polymer carrier.

Ideally, however, the nature of $R^4$, and moreover of $R^2$ in general should be such that cross-reactivity with $R^1$, $X^1$, and $X^2$ is avoided.

In other embodiments of the invention, the terminus of the linking unit is a functional group deemed suitable for activation for coupling to a polymer carrier. That is to say that the functional group must first be activated by chemical modification prior to being covalently linked to the polymer carrier. In such embodiments, the terminus of the linking unit is any functional group that can be readily activated by methods known by the person skilled in the art. Such functionalities can be selected from the group comprising of amines, carboxylic acids, thiol, hydroxyl and so forth. The person skilled in the art can easily envisage a multitude of functional groups that are suitable for activation, means of activation, as well as means of covalently linking the activated system to a polymer carrier.

In embodiments where the linking unit must first be activated by chemical modification prior to covalent linkage to the polymer carrier, $R^4$, the terminus of the linking unit suitable for activation can be a function group selected from the group comprising of amines, carboxylic acids, thiol, hydroxyl and any functional group that can be readily activated by methods known by the person skilled in the art.

In certain embodiments, a covalent bond between the linker unit and an amine present on a polymer carrier, such as a protein, the terminus of the linker unit is a carboxylate or a carboxylic acid. In a preferred embodiment of the invention, the terminus of the linker unit of the hapten, such as $R^4$, comprises of a carboxylic acid, which can be readily activated for coupling for immunisation purposes. Activation can be done by modifying the carboxylic acid to an activated form of a carboxyl such as, but not exclusively, to its corresponding acyl halide, anhydride, activated esters such as succinimidyl esters. The coupling of the linking unit may also be to groups other than amines present on a polymer carrier such as thiols and hydroxyls.

In preferred embodiments if this assay, the linking unit moiety is not pre-activated for coupling to a polymer carrier. In such systems, the terminus of the linker unit, such as $R^4$, is a carboxylic acid, an amine, a thiol, or a hydroxyl. In embodiments wherein the polymer carrier is a protein or polyamide, the terminus of the linker unit, such as $R^4$, is preferably a carboxylic acid, an amine, a thiol, or a hydroxyl, particularly an amine or carboxylic acid.

In another embodiment of this aspect of the invention, the terminus of the linking unit $R^4$ is selected from a group comprising of amine, hydroxyl and thiol. These groups can couple to a carboxylate, carboxylic acid, or any form of a carboxyl, including activated forms, present on the polymer carrier. Preferred embodiments of this aspect of the invention, an amine functionality at the terminus of the linking unit is used to couple to a carboxylate, carboxylic acid, or any form of a carboxyl, including activated forms, present on the polymer carrier.

Prior to immunisation, the haptens must be conjugated to a polymer carrier, such as to a protein, for e.g. ovalbumin (OA). As stated above, in certain embodiments, conjugation may require preliminary activation of the terminal carboxyl of the linking unit (i.e. in non pre-activated systems). As is known by the person skilled in the art, activation of the carboxyl can be done using common peptide coupling reagents (see for e.g. M. Bodansky and A. Bodansky, *The Practice of Peptide Synthesis*, 2. Ed, Springer-Verlag, 1994, J. Jones,, "The Chemical Synthesis of Peptides", Clarendon Press, 1991).

As described in Example 3, non pre-activated haptens in which the terminus of $R^2$, i.e. $R^4$, was a carboxylic acid were activated for coupling using reagents such as BOP and DCC and the appropriate additives and reagents. The activated hapten was reacted to a polymer carrier to form a hapten-polymer carrier complex prior to immunisation.

As is known by the person skilled in the art, the number of haptens bound to each polymer carrier can vary dramatically according to the conditions employed in the coupling process. Also, the type of polymer carrier used can influence the number of haptens bound to each polymer carrier. In preferred embodiments, the number of haptens per polymer carrier range from 1:1 to 50:1, such as 1:1 to 5:1, 2:1 to 10:1, 5:1 to 20:1, 10:1 to 30:1, 20:1 to 40:1, or 30:1 to 50:1. In one particular embodiment, the hapten per polymer carrier ratio was 5:1 with respect the number of moles of the hapten N-(5-carboxypentyl)-2,4-dichloro-3-amido aniline (EQ-0031) bound to the protein ovalbumin.

ii) The length and position of linking unit moiety

The present investigators have found that the position of the linking unit is critical to the ability of the hapten to raise antibodies suitable for the analysis of BAM (vide infra).

Specifically, the position of $R^2$ relative to $R^1$ (and in turn to $X^1$ and $X^2$) may be critical to appropriately orient the hapten for recognition by an antibody during immunisation. The inventors have critically determined that compounds where $R^2$ (as opposed to $R^1$) serves as the linking unit moiety are suitable to raise antibodies for the analysis of dichlorbenil and chlorthiamid degradation products. Thus $R^2$ is in the meta position relative to $R^1$.

As stated, the linking unit moiety must be in the meta position relative to $R^1$. The importance of the position of the linking unit was illustrated in cases where immunisations with haptens in which $R^1$ itself served as a linking unit (for instance, where the amide group of BAM was chemically extended in such as way as to yield succinimidyl-N-(2,6-dichlorobenzoyl)-6-amino-hexanoate, a pre-activated hapten (EQ-0025)). In such a case, the hapten was able to induce strong immunoresponse and several clones were generated. However, and most notably, none of the produced antibodies were able to detect free dichlorbenil nor its main degradation product, namely BAM, the preferred test analyte. This result highlights the importance of the position of the linking unit. This phenomenon clearly indicates that the antibodies have linking unit-specificity with regards to the linking unit's position on the ring. This also implies that the antibodies may be recognising the linking unit (or at least a part thereof) as well as the ring structure. Thus neither $X^1$ and $X^2$ were used to link to the polymeric carrier.

The linker unit can consist of a variety of chains, including, but not limited to esters, amides, ethers, thioethers, and secondary amines. The linking unit moiety, $R^2$ is of a length appropriate to suitable orient the hapten relative to the polymer carrier to create a recognition motif for an antibody.

Currently believed to be of critical importance for appropriate orientation of the hapten molecule are the flexibility and length of the linking unit component, $R^2$. The linking unit serves to orient the hapten for recognition by the antibody. The linking unit, $R^2$, in formula I, is preferably in the range of 3 to 25 atoms in length, excluding the atoms of $R^4$, particularly ranging form 3–15 atoms in length. Alternatively, the length can be viewed in absolute empirical terms, namely as being between 5 and 75 Å, preferably no more than 50 Å.

Present understanding of such systems is that for appropriate orientation of the hapten molecule, the flexibility and length of the linking unit component, $R^2$ are extremely pertinent. Given that $R^2$ can be selected from the group consisting —C(=O)—N($R^5$)—($CH_2$)$_n$—$R^3$—($CH_2$)$_m$—$R^4$, —N($R^5$)—C(=O)—($CH_2$)$_n$—$R^3$—($CH_2$)$_m$—$R^4$, —O—($CH_2$)$_n$—$R^3$, —($CH_2$)$_m$—$R^4$, —N($R^5$)—($CH_2$)$_n$—$R^3$—($CH_2$)$_m$O—$R^4$, —S—($CH_2$)$_n$—$R^3$—($CH_2$)$_m$$R^3$—($CH_2$)$_m$—$R^4$, —($CH_2$)$_{n+1}$—$R^3$—($CH_2$)$_m$—$R^4$, —C(=O)—O—($CH_2$)$_n$—$R^3$—($CH_2$)$_m$—$R^4$ and —O—C(=O)—($CH_2$)$_n$—$R^3$—($CH_2$)$_m$—$R^4$, the flexibility of the linking unit is regulated to a great extent by the nature of $R^3$ and by the size of the terms m and n. In one embodiment, n and m are independent and are integers from 0 to 8. The greater the independent values and the greater their added values, the greater the length and flexibility of the linking unit. Their independent values can, in one embodiment, be as low as 0 resulting in a short linking unit moiety. Their added values (m+n), can range from 0 to 16, preferably being between 0 and 12, such as 12, 11, 10, 9, 8, 7, 6, 5, 4, 3, 2, 1, and 0. Linking units having a total number of atoms between the aromatic moiety (formula I), and $R^4$ in the range of 3–25 (not inclusively), such as in the range of 3–15, are believed to be particularly interesting.

In one embodiment of the invention, $R^2$ is linked to the aromatic portion of hapten used for immunisation by an amide bond. The linkage can be either as the C-terminus or N-terminus of an amide bond (ie the carbon of the carbonyl portion of the amide bond is bound to the aromatic ring or the amine portion of the amide bond is bound to the aromatic ring of the hapten used for immunisation). Haptens from both embodiments have generated immune response in live animals. In the preferred embodiments the amine of the amine bond is bound to the ring.

The nature of $R^3$ may also be of critical importance for appropriate orientation of the hapten molecule influencing the flexibility and length of the linking unit component. $R^3$ is selected from the group consisting of —O—C(=O)—, —C(=O)—O—, —O—C(=S)—, —C(=S)—C—, N($R^5$)—C(=O)—, —C(=O)—N($R^5$)—, —O—, —N($R^6$)—, optionally substituted $C_{1-4}$ alkylene, optionally substituted arylene, optionally substituted heteroarylene, an optionally substituted $C_3$–$C_7$ cycloalkylene.

Some functionalities, such as when $R^3$ is a ring system (be they optionally substituted arylene, optionally substituted heteroarylene, an optionally substituted $C_3$–$C_7$ cycloalkylene) instill rigidity to the system. Other functionalities, such as when $R_3$ is selected from —O—, —S—, C(=O)—, —C(=O)—O—, —O—C(=S)—, —C(=S)—O—, —N($R^6$)—C(=O)—, —C(=O)—N ($R^5$)— cause variations in both the flexibility and orientation by causing a bend in a linking unit.

In preferred embodiments of the invention, $R^3$ is selected from the group consisting of optionally substituted $C_{1-4}$ alkylene, optionally substituted $C_{3-7}$ cycloalkylene, optionally substituted aromatic and optionally substituted heteroarylene, in particular selected from optionally substituted $C_{1-4}$ alkylene and optionally substituted $C_{3-7}$ cycloalkylene, most particularly is $C_{1-4}$ alkylene.

In the embodiment whereby $R^3$ is selected from —N($R^5$)—, $R^5$ is selected from hydrogen, optionally substituted $C_{1-4}$ alkyl, optionally substituted $C_{2-5}$ alkenyl, optionally substituted $C_{2-8}$ alkynyl, optionally substituted aryl, optionally substituted heteroaryl, and optionally substituted $C_3$–$C_7$ cycloalkyl. In preferred embodiments, $R^5$ consists of hydrogen, optionally substituted $C_{1-4}$ alkyl, optionally substituted $C_{2-5}$ alkenyl and optionally substituted $C_{2-8}$ alkynyl, preferably from hydrogen and optionally substituted $C_{1-4}$ alkyl.

iii The Polymer Carrier

As previously stated, prior to immunisation the hapten is coupled to a polymer carrier. As in known by the person skilled in the art, any number of polymer carriers are suitable for generating an immunoresponse in the immunisation procedure (see Christopher P. Price and David J. Newman eds., *Principles and Practice of Immunoassay*, second edition, p. 35–64, Macmillan Reference Ltd., 1997, London, U.K.). The polymer carrier can be selected from any carrier which elicits an immune response including but not limited to polyamides, proteins, nucleic acids, polynuclueotides, glycans, dextrans, peptido-glycans, lectins, glutins. The person skilled in the art is aware that the immunisation process can be accomplished by innumerable means using a hapten and a polymer carrier of sorts. In some preferred embodiments, the polymer carrier is a protein. Proteins may typically be selected from a group comprising of Ovalbumin (OA), Bovine Serum Albumin (BSA); Keyhole Limpet Haemocyanin (KLH), Purified Protein Derivative (PPD, derived from Mycobacterium tuberculosis), thyroglobulin, albumin, streptavidin and avidin, notably OA and PPD, BSA, and KLH.

b) The Aromatic Moiety

The present investigators have found that $R^1$ comprises at least part of one of the recognition sites, i.e. is part of the recognition motif, by the antibody in the immunisation process. $R^1$ is selected from group comprising of —C(=O)—N($R^5$)($R^5$), —N($R^5$)—C(=O)—O$R^5$, —C(=O)—O$R^5$, —N($R^5$)—C(=O)($R^5$), —N($R^5$)—C(=S)($R^5$), —C(=S)—N($R^5$)($R^5$), —N($R^5$)—C(=S)—N ($R^5$)$R^5$), —N($R^5$)—C(=O)—N($R^5$)($R^5$), —O—C(=O)—$R^5$, —C(=S)—O$R^5$, —O—C(=S)—$R^5$, —O—$R^5$, —N($R^5$)($R^5$), —S—$R^5$, —$CH_2$—$R^5$, —CN, and halogen; wherein $R^5$ is independently selected from the group consisting of hydrogen, optionally substituted $C_{1-4}$ alkyl, optionally substituted $C_{2-5}$ alkenyl, optionally substituted $C_{2-8}$ alkynyl, optionally substituted aryl, optionally substituted heteroaryl, and optionally substituted $C_3$–$C_7$ cycloalkyl, such as —C(=O)—N($R^5$)($R^5$) —N($R^5$)—C (=O)—O$R^5$, —C(=O)—O$R^5$, —O—C(=O)—$R^5$, —C(=S)—O$R^5$, —O—C(=S)—$R^5$, —O—$R^5$, —N($R^5$)($R^5$), —S—$R^5$, —$CH_2$—$R^5$, —CN, and halogen. Preferred embodiments of the invention are those where $R^1$ is —C(=O)—N($R^5$)($R^5$), —C(=S)—N($R^5$)(R), —N($R^5$)—C(=O)—O$R^5$ and —CN, preferably —C(=O)—N($R^5$)($R^5$), —C(=S)—N($R^5$)($R^5$) and CN, in particular —C(=O)—$NH_2$ (i.e. where both $R^5$ groups are hydrogen).

$R^1$ is situated between $X^1$ and $X^2$. In one embodiment of the invention, $X^1$ and $X_2$ are as present in one of the principal test analytes, BAM; i.e. both $X^1$ and $X^2$ are chlorine. However, $X^1$ and $X^2$ need not be identical. In another embodiment of the invention, $X^1$ is chlorine and $X^2$ is selected from bromine, fluorine and iodine; alternatively, $X^2$ is chlorine and $X^1$ is selected from bromine, fluorine and iodine. In an interesting embodiment of the invention, both $X^1$ and $X^2$ are independently selected from halogens other than those present in one of the principal test analyte (BAM), such as bromine, fluroine or iodine.

In a combination of preferred embodiments, $X^1$ is chlorine, $X^2$ is chlorine, and $R^1$ is C(=O)—$NH_2$.

One means by which the importance of the nature of $R^1$ can be illustrated is by the comparison of the suitability of two haptens that differ solely in the nature of $R^1$. When the hapten N-(5-Carboxypentyl)-2,4-dichloro-3-amido aniline (EQ-0031) bound to the protein ovalbumin was used for immunisation purposes, good responses were generated and several clones were produced. One of these clones (HYB 273-1) has been found to be suitable to generate monoclonal antibodies for the use of an immunoassay for BAM. Immunisations with a hapten (EQ-0030) in which the linking unit $R^2$, is in the same position (meta) to $R^1$ and of the same length as that used in EQ-0031, but where the ring substituents ($X^1$, $X^2$, and $R^1$) are modified only in that $R^1$ is a nitrile (CN) instead of an amide {—C(=O)—NH$_2$)} were not able to induce appropriate immunoresponses. No suitable antibodies were generated. This result indicates that the judicious choice of $X^1$, $X_2$ and $R^1$ are crucial for generating antibodies appropriate for the immunoassay of dichlorbenil and chlorthiamid and their derivatives and degradation products.

In an exemplary embodiment of the method according to the present invention monoclonal antibodies generated from the clone HYB 273-1, in turn generated from immunisations with hapten EQ-0031 were, as stated above, used in homologous competitive immunoassays for BAM. These antibodies demonstrated excellent selectivity showing very little cross-reactivity (less than 10.8%) with other analytes of similar structural composition (see Table 3). The cross-reactivity is determined by dividing the IC$_{50}$ (vide infra) of the desired analyte (in this case BAM) by the IC$_{50}$ of the test analyte and multiplying the total by 100.

The above example is not intended to be limiting in any way. Any complex according to the present invention may be used to raise antibodies. Antibodies raised from a complex according to the present invention may be used in the present invention The cross reactivity of an assay is a measure of its specificity for the analyte relative to similar or related compounds. It is useful in assessing its accuracy in crude samples with several potential haptens. Standard curves based on the 4-parameter-logistic equation (eq 1) were generated for a series of analytes (Table 3) in the range 100 to 0 mg/L (10-fold titrations). The IC$_{50}$ value (C*) for each analyte was then compared with the IC$_{50}$ of BAM (C) in equation 3.

$$CR = \left(\frac{C}{C^*}\right) \times 100\% \quad (3)$$

As can be seen by Table 3, the assay in which HYB 273-1 was used as a antibody, showed very high specificity for BAM. The highest cross-reactivity was with 2,4-dichlorobenzamide at 3.8%. There was no measurable cross-reactivity with the parent compound, dichlorbenil.

In preferred embodiments, the complex of N-(5-carboxypentyl)-2,4-dichloro-3-amido aniline and a protein serves to raise antibodies. The use of antibodies raised from the N-(5-carboxypentyl)-2,4-dichloro-3-amido aniline-protein is demonstrated in the Examples, such as antibodies cloned from HYB-273-1. However, as is known by the person skilled in the art, any antibody raised from a complex according to the present invention may be suitable for an assay according to the present invention.

As was discussed earlier, when $R^1$ of the hapten exists as an amide which was homologated into a linking unit (succinimidyl-N-(2,6-dichlorobenzoyl)-6-amino-hexanoate, hapten EQ-0025), assay results were poor. Quite surprisingly however, immunisations with haptens in which the same linking unit as that used in EQ-0025 is in the meta-position with respect to the amide of BAM (such as EQ-0031), generated good immunoresponse and clones produced were used to generate monoclonal antibodies (as stated above) by the methods known by a person skilled in the art. Some of these cloned antibodies (such as HYB 273-1) have excellent specificity for the analyte BAM and are useful for immunoassays of type embodied in this invention. These results, on their own and when compared to results in which no immunoresponse was produced, indicate that the position and/or size of the linking unit are crucial for generating antibodies applicable to the immunoassay of dichlorbenil and chlorthiamid degradation products.

Live mice were primed for immunisation by an intraperitoneal injection of live BCG-vaccine one month before immunisation. The antigen (hapten-OA complex), once adsorbed onto Al(OH)$_3$, was injected intraperitonally and test bleeding were collected. When antibody titre's exceeded 1:2000, mice were considered ready for fusion and the method described by Köhler and Milstein (1975) was employed with minor modifications. Monoclonal antibodies were selected on basis of titre, affinity and specificity. Selected clones were recloned until monoclonality and stored frozen at −80° C.

II. The Compound Used for Immobilisation i) The Hapten and Assay Types

In interesting embodiments of the method according to the present invention, the assays are adapted for high throughput screening. The assays may comprise but are not limited to assays utilising radioligand binding, using scintillation proximity assays; and fluorescence technologies such as time-resolved fluorescence, fluorescence resonance energy transfer, and fluorescence polarisation.

The immunoassay utilised in the identification or quantification of any of the degradation products of dichlorbenil and chlorthiamid may be, for example, a homogeneous immunoassay or a heterogeneous immunoassay procedure (see Christopher P. Price and David J. Newman eds., *Principles and Practice of Immunoassay,* second edition, p. 35–64, Macmillan Reference Ltd., 1997, London, U.K.).

In a heterogeneous immunoassay, an immobilised hapten is attached to an insoluble matrix. A heterogeneous assay involves the separation of the unbound antigen in a liquid phase from the bound hapten (on the solid phase). In a preferred embodiment of the invention, the assay is heterogeneous. Furthermore, in this preferred embodiment of the invention, the hapten used to raise antibodies in the animal is also the hapten used for immobilisation onto the solid support. This is known as a homologous (heterogeneous) competitive assay, as is known by the person skilled in the art.

In an alternative embodiment of a heterogeneous immunoassay, the antibody is immobilised to the solid support.

In embodiments wherein the immunoassay used for the identification or quantification of the degradation products of dichlorbenil and chlorthiamid is homogeneous, a solid phase support is not utilised but rather the assay completely solution based. In homogenous assays, all reagents are in the same phase and the reaction is not stopped and assay parameters are measured when the assay system has reached a steady state. They do not require a phase separation whereby the "free" reagents are washed from those "bound". In such an assay, the hapten is labelled with an enzyme and to this is added sample containing an unknown concentration of the analyte. An antibody specific to the hapten (and analyte if they are different, i.e. a heterologous homogeneous assay) is then added and the antibody binds to the enzyme-labelled hapten and to the analyte. The interaction between the antibody and the hapten results in the inhibition of the enzymatic activity of the label. A suitable substrate for the enzyme label is added and spectrophotometric analysis of the samples, once compared to the response of known concentrations of the analyte standards, produces a quantifiable result.

In embodiments wherein the hapten is immobilised to the solid support, the linking unit, $R^2$, serves to couple the hapten to the solid support. This linking unit can be a pre-activated system or activated as described for the coupling of the hapten to a polymer carrier in the immunisation process. The hapten used for immunisation can itself be bound to the solid support. Conversely, this hapten can be immobilised to the solid support via a polymer carrier. In the latter case, the activated or pre-activated hapten is first coupled to the polymer carrier to form a hapten-polymer complex. This complex is immobilised to the solid support matrix for the purpose of the assay.

One embodiment of the method entails what a person skilled in the art knows as a sandwich assay. In this case, an antibody raised from the hapten-polymer carrier complex is immobilised on the solid phase. A sample containing the analyte is added an allowed to bind to the antibody. After appropriate incubation time and washing, a suitably labelled antibody is added to the solid phase and allowed to incubate and specifically bind to the analyte such that the analyte is sandwiched between two antibodies specific for it. All unbound labelled antibody is washed away. Enzymatic substrate is then added and colorimetric analysis allows for comparison to a standard procedure (see Christopher P. Price and David J. Newman eds., *Principles and Practice of Immunoassay*, second edition, p. 35–64, Macmillan Reference Ltd., 1997, London, U.K.).

In a preferred embodiment of the invention, the hapten used for immobilisation is modified (relative to the hapten used for immunisation) such that the affinity of an antibody is shifted from the immobilised hapten to the analyte, which resembles the hapten utilised for immunisation. Such an immunoassay is called a heterologous competitive assay and is more sensitive than the homologous competitive immunoassay.

Of course, in scenarios where the hapten used for immunisation is different to that used for immobilisation (a heterologous assay), the antibodies raised from particular hapten must be able to recognise the immobilised hapten as well as the test analyte. An immobilised hapten of the general formula II allows for greater affinity for the intended analytes (i.e. degradation products of dichlorbenil and chlorthiamid) by antibodies raised from haptens of the general formula I. The immobilised hapten can differ in that it comprises of a heteroaromatic ring, in the judicious choice of substituents around the ring, and in the choice of linking unit. Alteration of the ring system and ring periphery allows for attenuation as to the sensitivity of the assay.

As it has been discussed, the hapten used for immobilisation need not necessarily be identical to the hapten used for immunisation (heterologous assay). An assay in which the affinity of the antibody is higher for the analyte than for the immobilised hapten is more sensitive than its homologous counterpart. It allows for an exploitation of a more diverse range of haptens utilised for immobilisation. One can conceive of immobilised haptens consisting of, for instance, substitution not only of the groups attached to the ring, i.e. $X^1$, $X^2$, $R^1$, $R^2$ of formula I, but also to the ring itself, insofar as that the immobilised hapten comprises of a heteroaromatic rings, to comprise of haptens of the general formula II.

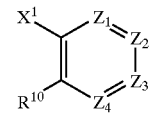

II

In this embodiment, a method for an immunoassay has a hapten of the general formula II immobilised to a solid support; wherein $Z_1$ is selected from C—$R^8$ or nitrogen, $Z_2$ is selected from C—$R^7$ or nitrogen, $Z_3$ is selected from C—$R^8$ or nitrogen, $Z_4$ is selected from C—$R^9$ or nitrogen, where at least one of $R^6$–$R^{10}$ is present and serves as a linking unit for immobilisation of the hapten to the solid support, and the ones of $R^6$–$R^{10}$ which are present and do not serve as a linking unit are independently selected from a group consisting of —C(=O)—NH$_2$, —N($R^5$)($R^5$), —N($R^5$)—C(=O)($R^5$), —N($R^5$)—C(=S)($R^5$), —C(=S)—N($R^5$)($R^5$), —N($R^5$)—C(=S)—N($R^5$)($R^5$), —N($R^5$)—C(=O)—N($R^5$)($R^5$), —CN, —C(=O)—N($R^5$)($R^6$), —N($R^5$)—C(=O)—O$R^5$, —N($R^5$)—C(=O)—O$R^5$, —C(=O)—O$R^5$, —O—C(=O)—$R^5$, —C(=S)—O$R^5$, —O—C(=S)—$R^5$, hydrogen, and halogen; where $X^1$ is selected from halogens, and where $R^5$ is independently selected from the group consisting of hydrogen, optionally substituted $C_{1-4}$ alkyl, optionally substituted $C_{2-5}$ alkenyl, optionally substituted $C_{2-6}$ alkynyl, optionally substituted aryl, optionally substituted heteroaryl, and optionally substituted $C_3$–$C_7$ cycloalkyl.

The compound used for immobilisation can comprise of a heteroaromatic moiety, according to general formula II, which can comprise of up to 4 heteroatoms in the ring. In one embodiment, the number of heteroatoms is less than 4, such as less than 3, such as 2, or preferably 1 or 0. The position of the heteroatom relative to the fixed position of the carbon bound to $X^1$ may play an important role in the ability of the immobilised hapten to be recognised by the antibody raised from a hapten of the general formula I. In a another embodiment, no two neighbouring atoms are heteroatoms. In another preferred embodiment $Z_1$–$Z_4$ respectively consist of C—$R^8$ to C—$R^9$, that is to say, the ring is not heteroaromatic.

The groups $R^8$–$R^{10}$ serving as linking units can be independently selected from the group consisting of —C(=O)—N($R^5$)—(CH$_2$)$_n$—$R^3$—(CH$_2$)$_m$—$R^4$, —N($R^5$)—C(=O)—(CH$_2$)$_n$—$R^3$—(CH$_2$)$_m$—$R^4$, —O—(CH$_2$)$_n$—$R^3$—(CH$_2$)$_m$—$R^4$, —N($R^5$)—(CH$_2$)$_n$—$R^3$—(CH$_2$)$_m$—$R^4$, —S—(CH$_2$)$_n$—$R^3$—(CH$_2$)$_m$—$R^4$, —(CH$_2$)$_{n+1}$—$R^3$—(CH$_2$)$_m$—$R^4$, —O—C(=O)—(CH$_2$)$_n$—$R^3$—(CH$_2$)$_m$—$R^4$, and —O—C(=O)—(CH$_2$)$_n$—$R^3$—(CH$_2$)$_m$—$R^4$ wherein n and m independently are integers from 0 to 8; where $R^3$ is selected from the group consisting of —O—C(=O)—, —C(=O)—O—, —O—C(=S)—, —C(=S)—O—, —N($R^5$)—C(=O)—, —C(=O)—N($R^5$)—, —O—, —S—, —N($R^5$)—, optionally substituted $C_{1-4}$ alkylene, optionally substituted arylene, optionally substituted heteroarylene, an optionally substituted $C_3$–$C_7$ cycloalkylene; where $R^4$ is selected from the group consisting of activated forms of a carboxyl, carboxylic acid, amine, acyl halides, activated esters, thiols, disulphides (—S—S—R), halides, sulphonates, quinones and imides; and where $R^5$ is independently selected from the group consisting of hydrogen, optionally substituted $C_{1-4}$ alkyl, optionally substituted $C_{2-5}$ alkenyl, optionally substituted $C_{2-6}$ alkynyl, optionally substituted aryl, optionally substituted heteroaryl, and optionally substituted $C_3$–$C_7$ cycloalkyl.

Given that no fewer than 1 of $R^6$–$R^{10}$ are selected from the group consisting of of —C(=O)—N($R^5$)—(CH$_2$)$_n$—$R^3$—(CH$_2$)$_m$—$R^4$, —O—(CH$_2$)$_n$—$R^3$—(CH$_2$)$_m$—$R^4$, —N($R^5$)—(CH$_2$)$_n$—$R^3$—(CH$_2$)$_m$—$R^4$, —N($R^5$)—C(=O)—(CH$_2$)$_n$—$R^3$—(CH$_2$)$_m$—$R^4$, —S—(CH$_2$)$_n$—$R^3$—(CH$_2$)$_m$—$R^4$, —CH$_2$—(CH$_2$)$_n$—$R^3$—(CH$_2$)$_m$—$R^4$, —O—C(=O)—(CH$_2$)$_n$—$R^3$—(CH$_2$)$_m$—$R^4$, and —O—C(=O)—(CH$_2$)$_n$—$R^3$—(CH$_2$)$_m$—$R^4$, the potential of linking units is as much as 4. In preferred embodiments, fewer than 3 of $R^6$–$R^{10}$ serve as linking units, particularly fewer than 2, namely preferably 1.

In preferred embodiments, one of $R^6$–$R^{10}$ is a linking unit selected from the group consisting of —C(=O)—NH—(CH$_2$)$_n$—$R^3$—(CH$_2$)$_m$—$R^4$ and —NH—C(=O)—(CH$_2$)$_n$—$R^3$—(CH$_2$)$_m$—$R^4$, particularly from —NH—C(=O)—(CH$_2$)$_n$—$R^3$—(CH$_2$)$_m$—$R^4$.

The terminus of the linker unit $R^6$–$R^{10}$, such as $R^4$, is a functional group suitable for chemo-, photo-, electro- or thermo-reactivity and combinations thereof. The terminus of the linker unit or $R^4$ as such, can be selected from the group comprising of activated forms of a carboxylates, carboxylic acid, amine, acyl halides, activated esters, thiols, disulphides (—S—S—R), halides, sulphonates, quinones and imides. Alternatively, as discussed infra, the terminus of the linker unit or $R^4$ as such can be a group suitable for activation such as a carboxylic acid, amine, thiol, or hydroxyl. However, as is known by the person skilled in the art and as discussed infra, the covalent linking of two components can be accomplished by countless methods too numerous to describe or enumerate.

Those of $R^6$–$R^{10}$ not serving as linking units are selected from a group comprising of —C(=O)—NH$_2$, —N($R^5$)($R^5$), —N($R^5$)—C(=O)($R^5$), —N($R^5$)—C(=S)($R^6$), —C(=S)—N($R^5$)($R^5$), —N($R^5$)—C(=S)—N($R^5$)($R^5$), —N($R^5$)—C(=O)—N($R^5$)($R^5$), —CN, —N($R^5$)—C(=O)—O$R^5$, —C(=O)N($R^5$)($R^5$), —C(=O)—O$R^5$, —O—C(=O)—$R^5$, —C(=S)—O$R^5$, —O—C(=S)—$R^5$, hydrogen and halogen. In one embodiment, at least two of $R^6$–$R^{10}$ not serving as linking units are selected from a group comprising —C(=O)—NH$_2$, —N($R^5$)($R^5$), —C(=O)—N($R^5$)($R^5$), —($R^5$)—C(=O)—O$R^5$, —C(=O)—O$R^5$, —O—C(=O)—$R^5$, —C(=S)—O$R^5$, —O—C(=S)—$R^5$, —N($R^5$)—C(=O)($R^5$), —N($R^5$)—C(=S)($R^5$), —C(=S)—N($R^5$)($R^5$), —N($R^5$)—C(=S)—N($R^5$)($R^5$), —N($R^5$)—C(=O)—N($R^5$)($R^5$), —CN and halogen. Within this embodiment, those $R^6$–$R^{10}$ not serving as linking units are preferably selected from —C(=OH)—NH$_2$, —C(=O)—N($R^5$)($R^5$), —N($R^5$)—C(=O)—O$R^5$, —N($R^5$)—C(=O)($R^5$), —N($R^5$)—C(=O)—N($R^5$)($R^5$), —CN, and halogen.

The number of halogens attached to the ring can be at most 4 (given that $X^1$ is a halogen and at least one must be a linking unit). In a preferred embodiments of the invention, the number of halogens bound to the ring of the hapten used for immobilisation is at most 3, preferably 2 or 1, preferably 2.

The number of hydrogens bound to the ring can be at most 4, preferably no more than 3, most preferably 2 or 1, preferably 2.

The preferred embodiments of $R^3$, $R^4$, $R^5$ and $X^1$ described for compounds used for the raising of antibodies also apply to compounds used for immobilisation. Thus, in a preferred embodiment, the compound used for immobilisation is for the general formula I.

Moreover, not only can the hapten used for immobilisation be different than that used for immunisation, but the polymer carrier to which the respective haptens are bound to form a hapten-polymer carrier complex may be different. They may be different in type, or of the same type but of different structure, as for e.g. one can be a protein, polyamide or polymer whilst the other is a glycan of sorts or they can both be proteins but one being OA and the other streptavidin or PBD or biotin. The polymeric carrier used in the immobilisation process may be the same as that used for immunisations but in preferred embodiments they are different.

Polymer carriers suitable for the immobilisation procedure can be selected from those deemed suitable for the immunisation procedure.

ii) Solid Support and Immobilisation

In a heterogeneous immunoassay, the hapten is linked either directly or indirectly (vide infra) to a solid support. The solid support can be agarose, cellulose, silicone-rubber, glass, plastic in many configurations such as polystyrene beads and polystyrene microtitre plates and any such support known to the person skilled in the art procedure (see Christopher P. Price and David J. Newman eds., *Principles and Practice of Immunoassay*, second edition, Macmillan Reference Ltd., 1997, London, U.K.). In preferred embodiments of the invention, the heterogeneous immunoassay involves the use of polystyrene beads or polystyrene microtitre plates, in particular polystyrene microtitre plates, as solid support.

The solid surface to which the hapten is immobilised can be selected from a wide variety of solid surfaces used in the analytical and diagnostic fields. Some more interesting types of solid surfaces are those of organic polymers, glasses, silicium and silicium oxide (silica) as well as composite materials thereof.

Among the organic polymers, polystyrene, polycarbonate, polypropylene, polyethylene, cellulose, nitrocellulose, agarose, polyethyleneglycol terephthalate, polyvinylacetate, polyvinyldifluoride, polymethylpentene, polyvinylpyrrolidinone, polyacrylate, polyacrylonitrile, polymethylmethacrylate and polyvinylchloride are illustrative examples, where polystyrene and polycarbonate are especially interesting examples.

Among the glasses and ceramics, borosilicate glass (Pyrex glass) and soda-lime glass are especially relevant examples, e.g. in the form of specimen tubes, vials, and slides for microscopy.

The body of the solid surface in itself may have a form or may be designed and shaped for the particular desired use; e.g. the body may be in the form of a sheet, a film, a bead, a pellet, a disc, a plate, a ring, a rod, a net, a membrane, a filter, a tray, a microplate (a microtitre plate), a stick, or a multi-bladed stick. Especially interesting bodies to be coated according to the present invention are microplates (microtitre plates), e.g. polystyrene microplates (microtitre plates), sticks, slides, tubes and beads.

Figure 3:
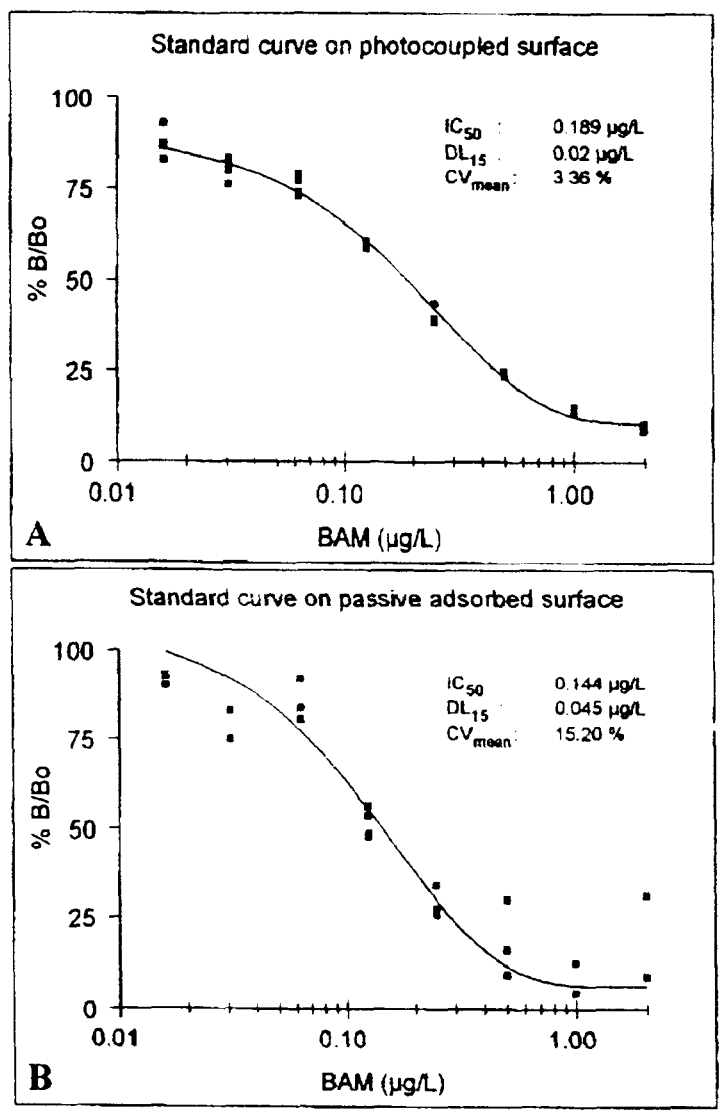
Figure 4:
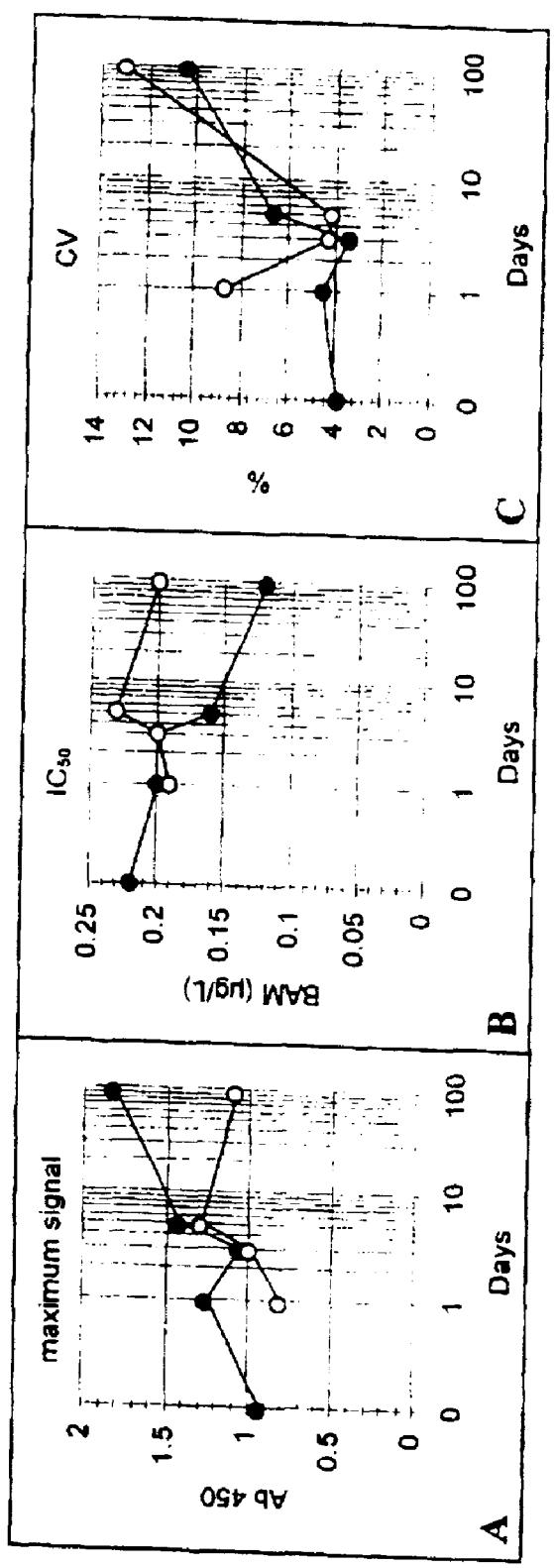

Immobilisation of the hapten to the solid support, either directly or via a polymer carrier, is accomplished by passive adsorption or covalent immobilisation by methods known to the person skilled in the art (Hermanson, 1992). In one embodiment of the immunoassay, the hapten is immobilised to a polystyrene microtitre plate by covalent immobilisation by means known to the person skilled in the art (see Example 1e). This immobilisation process is attractive in that it requires very little incubation time and was highly stable under dry storage (FIG. 4). In an alternative and particularly attractive embodiment of the method, the hapten is immobilised by passive adsorption. This adsorption process was also especially attractive in that immunoassays performed on these plates had an low coefficient of variation (CV), being less than 16% (FIG. 3). Preferred embodiments of the invention have CV values less than 20%.

As mentioned, the method of preparation of the microtitre plates varied depending of the method of immobilisation of the hapten. In a particularly attractive embodiment of covalent immobilisation (FIG. 2A), the immobilisation is performed through a photochemically active moiety, such as an anthraquinone moiety. This hapten, N-(5-carboxymethylpentyl)-2-anthraquinonecarboxamide (EQ-0028) was conjugated to a pre-existing hapten-protein complex (prepared in the usual manner between EQ-0031 and ovalbumin (OA)) to form hapten-OA-Anthraquinone conjugate complex. This complex was dialysed against PBS. Previous work by the applicant demonstrated that anthraquinones can be photocoupled to solid matrices by low energy photoactivation (PCT/DK 96/00167). Accordingly, a PolySorp plate was filled by a stationary dispensor with the hapten-OA-Anthraquinone conjugate. After exposing the plate to UV-light (300–400 nm) for 30 minutes, immobilisation was complete and the plate was washed and dried. The plate was either used immediately or sealed and stored at room temperature in the dark until use.

This latter method of immobilisation of complex, i.e. photocoupling via a conjugate complex comprising of anthraquinone, is a particular attractive embodiment. The anthraquinone moiety is directly coupled to the solid support and is linked through a polymer carrier to the hapten most directly accessible by an antibody. As was the case for haptens, the ratio of anthraquinone photocatalytic coupling moieties per polymer carrier molecule can range from 1:1 to 50:1. Preferred embodiments have said ratios no less than 2:1. In one particular embodiment where the anthraquinone photocatalytic coupler EQ-0028 was coupled to a pre-existing EQ-0031-OA complex (see Example 3), the ratio of EQ-0028 was 10 to 1 with respect to the number of moles of OA.

Passive adsorption (FIG. 2B) involved filling a Max-iSorp™ plate with a stationary dispensor with the hapten-OA conjugate. After coating overnight at 4° C., the plate was washed and dried. The plate was either used immediately or sealed and stored at room temperature in the dark until use.

As stated, the assays may be homogeneous or heterogenous. In embodiments wherein the immunoassay used for the identification or quantification of the degradation products of dichlorbenil and chlorthiamid is homogeneous, a solid phase support is not utilised but rather the assay completely solution based. In such an assay, the hapten is labelled with an enzyme and to this is added sample containing an unknown concentration of the analyte. An antibody specific to the hapten (and analyte if they are different, i.e. a heterologous homogeneous assay) is then added and the antibody binds to the enzyme-labelled hapten and to the analyte. The interaction between the antibody and the hapten results in the inhibition of the enzymatic activity of the label. A suitable substrate for the enzyme label is added and spectrophotometric analysis of the samples, once compared to the response of known concentrations of the analyte standards, produces a quantifiable result.

Standards were used to generate comparative standard curves. The standards were added to hapten-coated plates followed by a known amount of antibody, such as HYB 273-1 in buffer. The plate was incubated for 1 hour, washed, and incubated with $R\alpha M^{HRP}$, an enzyme label and incubated for 1 hour. After extensive washing, the enzyme substrate TMB-Plus was added. The colour development was stopped using acid and the absorbance read at 450 nm.

The standards were used to generate a semi-log graph based on the 4-parameter-logistic method (Rodbard, 1974: equation 1).

$$Y = \frac{(A-D)}{\left[1+\left(\frac{X}{C}\right)^B\right]} + D \qquad (1)$$

X: concentration of analyte (µg/L).
Y: absorbance at 450 nm ($A_{450}$).
A: maximum absorbance (upper asymptote).
D: minimum absorbance (lower asymptote).
C: midpoint between A and D. Extrapolation to x-axis yields the value of $IC_{50}$ (µg/L).
B: slope for the transition between A and D
The signals were normalised according to equation 2

$$\%\frac{B}{B_0} = \frac{A - A_{xs}}{A_0 - A_{xs}} \times 100 \qquad (2)$$

B: concentration of bound antibody and
$B_0$: concentration of bound antibody in the absence of analyte.

On the plot, 100% corresponds to the absorption of the zero control ($A_0$: 0 µg/L) and 0% corresponds to the absorption of an excess control ($A_{xa}$: 100 µg/L). The normalised signals were plotted vs. BAM concentration and the four-parameter-logistic equation (eq 1) was fitted to the experimental points.

The standard curves were prepared by quadruple determinations in order to also establish the coefficient of variation. The coefficient of variation is a reflection of the reliability of an assay. They are determined by the mean reading at a particular analyte concentration over repeated assays over a range of concentrations. FIG. 3 shows the variations of normalised readings of quadruple determinations for the standard curves for the plates which were covalently immobilised as compared to the plates in which passive adsorption was the means of adsorbing hapten. The $CV_{mean}$ for covalently immobilised plates was 3.36% whereas that for passive adsorption plates was 15.20%. Preferred embodiments of this immunoassay have CVs less than 20%. The immunoassays described by this invention using haptens of the general formula I to generate antibodies were performed on plates which were antigen-coated by either passive adsorption or covalent immobilisation showed excellent detection limits. Detection limits for either method of immobilisation ranged from 0.0156 to 2 µg/L. Detection limits are defined as $DL_{15}$ which quantifies the analyte concentration giving a 15% decrease in maximum signal. Thus, the lower the numerical value of the detection limit of the test, the better the performance of the test. Considering the EU limit of 0.1 µg/L for pesticides and their degradation products in drinking water, this assay is suitable for large-scale screening of samples of BAM. Preferred embodiments of the method according to the present invention have $DL_{15}$ values of most 0.1 µg/L, such as 0.1, 0.09, 0.08, or 0.06 µg/L, preferably at most 0.05 µg/L, such as 0.05, 0.04, 0.03, 0.02, or 0.01 µg/L.

The midpoint between the maximum and minimum adsorbance, referred to as the $IC_{50}$, indicates the concentration of analyte required causing a 50% signal reduction. It is a measure of the sensitivity of the assay. Again, the lower the numerical value of the $IC_{50}$, the better the performance of the assay. For the covalently immobilised plates, the $IC_{50}$ was found to be 0.189 µg/L whereas for passively adsorbed plates, the $IC_{50}$ was measured to be 0.144 µg/L. Considering the EU-limit of 0.1 µg/L for pesticides in drinking water, this immunoassay is suitable for large-scale screenings of water samples. Preferred embodiments of the invention have $IC_{50}$ values at most 0.5 µg/L, such as 0.5 or 0.4 µg/L, preferably at most 0.3 µg/L, such as 0.3, 0.2 µg/L.

Samples collected from 3 different water types were spiked with BAM. The samples were spiked with 0.05, 0.1, 0.5 and 1 µg/L of BAM and then analysed 4 times over 4 days (Table 2). The data showed that the assay was reliable over the investigative range (0.5 to 1 µg/L) and had an average inter-assay coefficient variation of 4.3%.

Of notable importance is the absence of significant matrix effects for the two ground water types as compared to the Milli-Q® water. Thus the assay lends itself readily to a variety of water types.

Figure 5:
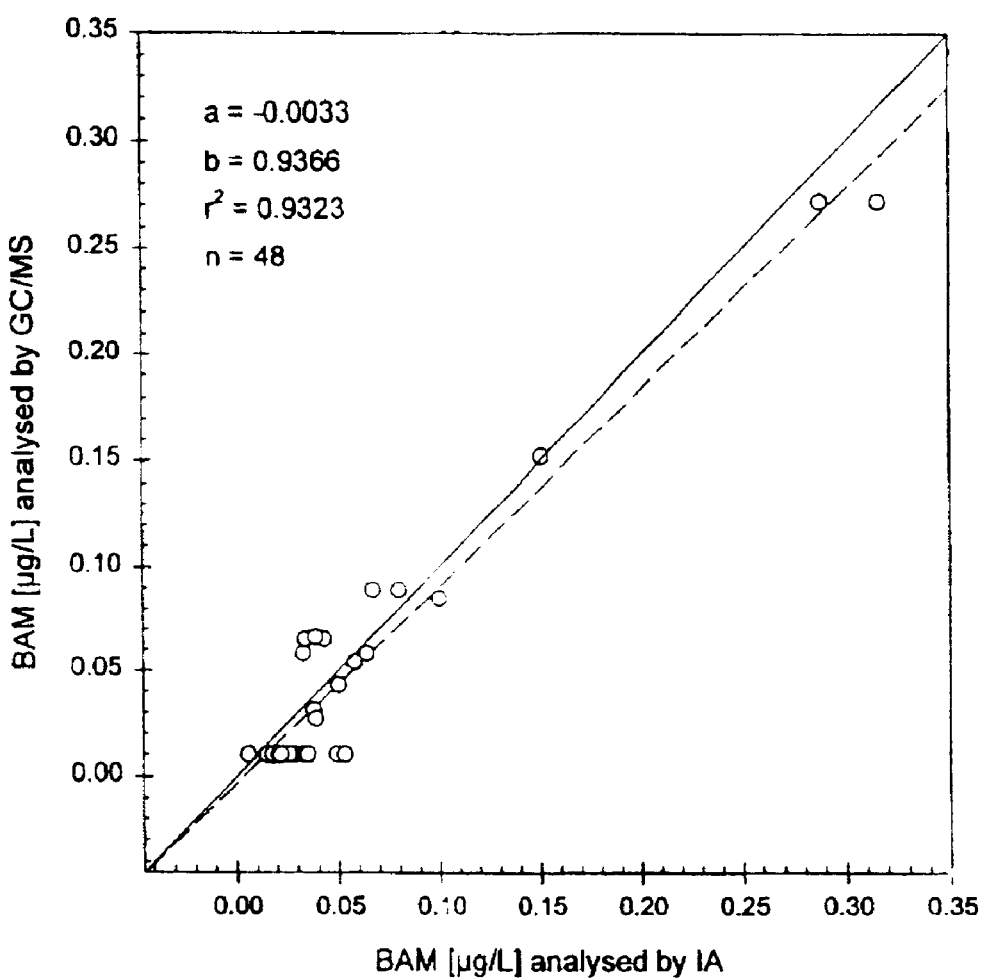

Samples of unknown concentrations were assayed and their concentrations were determined by comparing normalised absorbency readings to those on the standard curve. Assay results of these unknown samples were compared to concentrations as ascertained by the standard techniques of BAM analysis, i.e. HPLC and GC-MS and a comparative analysis is shown in FIG. 5. This comparative analysis demonstrates the accuracy and reliability of the assay as described by this invention.

III. The Analyte

The method described by the invention is for the identification or quantification of degradation products of pesticides that, in themselves, or whose degradation products are recognised by antibodies raised by antibodies from haptens as described infra. More particularly, the method is for the identification or quantification of dichlorbenil and chlorthiamid and their degradation products. This herbicide is degraded in the hydrosoil by biotic or abiotic processes. In one embodiment of the invention, the method is limited to the identification or quantification of its major degradation products 2,6-dichlorobenzamide (BAM), 3-hydroxy-2,6-dichlorobenzamide and its sugar conjugates and 4-hydroxy-2,6-dichlorobenzamide and its sugar conjugates. In preferred embodiments, the assay is limited to the identification or quantification of 2,6-dichlorobenzamide (BAM), 3-hydroxy-2,6-dichlorobenzamide and its sugar conjugates. Alternatively, the method is limited to the identification or quantification of 2,6-dichlorobenzamide (BAM), 3-hydroxy-2,6-dichlorobenzamide and 4-hydroxy-2,6-dichlorobenzamide. Most preferably, the method is for the identification or quantification of 2,6-dichlorobenzamide (BAM).

IV. Synthesis of Haptens

Haptens were synthesised using methods known by the person skilled in the art (Example 2). The synthesis generally involved the coupling of the a carboxylic acid portion of a linking unit chain moiety to an amino function of a substituted benzene, or conversely, coupling an amine function of a linking unit chain moiety to a carboxylic acid functionality of a substituted benzene ring, using traditional peptide coupling procedures including the use of such reagents as DCC (dicyclohexylcarbodiimide, or other suitable carbodiimides), BOP (including BOP Reagent and BOP-Cl) and the necessary additives in suitable solvents (see eg. M. Bodansky and A. Bodansky, "The Practice of Peptide Synthesis" 2. Ed. Springer-Verlag, 1994, J. Jones, "The Chemical Synthesis of Peptides", Clarendon Press, 1991).

V. Use of a Kit

In another aspect, the invention further relates to a kit for the immunological testing of pesticides, specifically to a kit for an immunoassay comprising a solid support and hapten as defined by formula II immobilised to the solid support. Moreover, the kit may further comprise an antibody raised from a hapten-polymer carrier complex as described by formula I.

BRIEF DESCRIPTION OF FIGURES AND TABLES

FIG. 1 Structures of the key-compounds used.

(A)-BAM is the primary metabolite of the pesticide dichlorbenil. (B)-The monoclonal antibodies were raised against the hapten EQ-0031 (N-(5-carboxypentyl)-2,4-dichloro-3-cyano aniline. (C)-The microtitre plates were covalent coated with ovalbumin conjugated with both EQ-0031 and EQ-0028. The anthraquinone EQ-0028 (N-(5-carboxypentyl)-2-antraquinoncarboxamide, was responsible for the photo-catalysed covalent immobilisation. (D)-BAM is a major degradation product of Casoron® and Prefix®. It may further degrade to 2,6-dichlorobenzoic acid.

Figure 2:
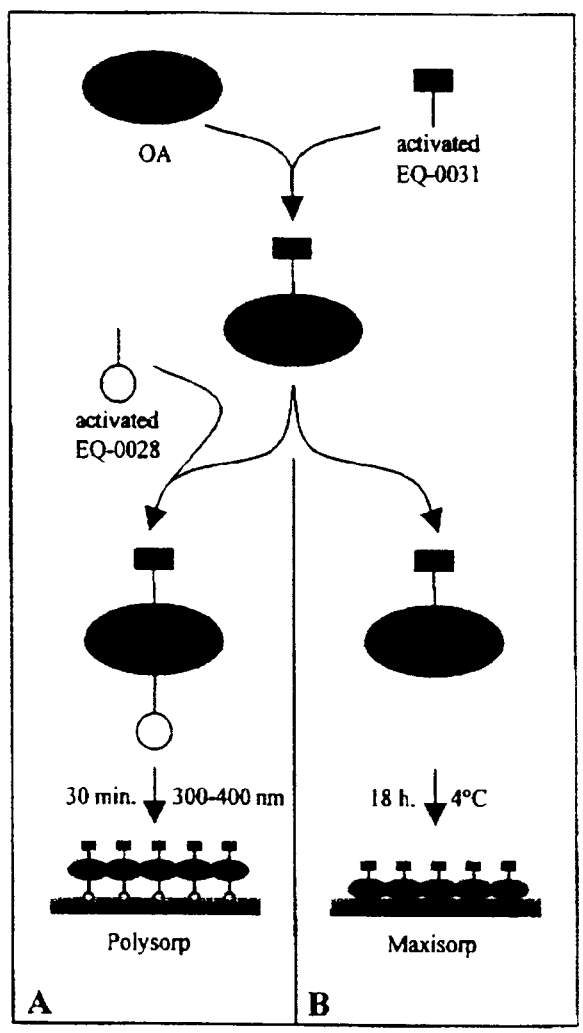

FIG. 2 Schematic illustration of the two immobilisation methods used in this work.

Ovalbumin (OA) was conjugated with EQ-0031 in a ratio of 1:5. This conjugate was either used directly for passive adsorption (B) or subsequently conjugated with EQ-0028 in a ratio of 1:10 for the use in covalent immobilisation (A).

FIG. 3 Standard curves for the BAM assay.

Standard curves were generated on either a photocoupled surface (PolySorp™: A) or a passive adsorbed surface (MaxiSorp™: B). $IC_{50}$ is the concentration of BAM for which the signal was decreased by 50 percent. $DL_{15}$ is the detection limit defined as the concentration of BAM that gives a decrease in signal by 15 percent. $CV_{mean}$ is the average of the variation of coefficient for each standard concentration. The assays were done by quadruplicate determinations.

FIG. 4 Performance of the assay on plates stored (dry) for up to 100 days at room temperature.

The stored plates were unsealed and evaluated by the generation of BAM standard curves. For each stored plate (back circles), one new freshly prepared plate was assayed as a reference (white circles). Maximum signal is the absorption measured on the negative standard (FIG. 4A). $IC_{50}$ is the concentration of BAM for which the signal was decreased by 50 percent (FIG. 4B). CV is the average of the CV's for each standard concentration, which were measured by quadruplicate determinations. (FIG. 4C).

FIG. 5 Comparative Analysis to GS/MS

Assay results of samples of unknown concentrations were plotted against concentration values as ascertained by the standard techniques of BAM analysis, i.e. GC-MS and a comparative analysis is shown in FIG. 5. This comparative analysis demonstrates the accuracy of the assay as described by this invention.

FIG. 6. Characteristics of the three water types used in the recovery assays.

The water from Ballerup (East-Denmark) was sampled from 3 meter depth in clay soil polluted by a landfill. The water from Vejen (West-Denmark) was sampled from 6.5 meter depth in sandy soil polluted by a landfill. None of the localities are known to be contaminated with BAM. The Dissolved Organic Carbon content, ion levels, and pH were determined for later evaluation of matrix effects.

FIG. 7. Recovery and precision studies on three different water types.

The water from Ballerup (East-Denmark) was sampled from 3 meter depth in clay soil polluted by a landfill. The water from Vejen (West-Denmark) was sampled from 6.5 meter depth in sandy soil polluted by a landfill. None of the localities are known to be contaminated with BAM. Each water type was spiked with the shown BAM concentrations and analysed as described in "Assay method". This was done four times with the same samples during four days. CV is the coefficient of variation between the four analyses of each sample.

FIG. 8. Cross-reactivity of the BAM assay for different BAM-related structures.

All the analytes were assayed in concentrations up to 100 mg/L. The calculation of the cross-reactivity for each analyte was done by dividing the $IC_{50}$ of BAM with the $IC_{50}$ of the analyte and then multiplying with 100. The names in brackets are the trivial names of the compound referred.

EXAMPLES

Example 1

General a) Reagents

Dichlorbenil [1194-65-6] and 2,6-dichlorobenzamide [2008-58-4] were from Riedel-de Haën (Seeize, Germany). Amiben [133-90-4], Kerb [23950-58-5] and 2,6-dichlorobenzoic acid [50-30-6] were from Labor Dr. Ehrenstorfer-Schäfers (Augsburg, Germany). O-chlorobenzamide [609-68-5], p-chlorobenzamide [619-56-7] and 2,6-dichloro-benzenemethanol [15258-73-8] were from Lancaster (Morecambe, England). Reagents for the synthesis of EQ-0031 and EQ-0028. Sodium chloride, potassium dihydrogen phosphate ($KH_2PO_4$), di-sodium hydrogen phosphate dihydrate ($Na_2HPO_4.2H_2O$), sodium hydrogen carbonate ($NaHCO_3$), di-sodium carbonate ($Na_2CO_3$), dimethylsulfoxide (HPLC quality, max 0.05% $H_2O$) and Tween 20 were from MERCK (Darmstadt, Germany). Benzotriazol-1-yloxy-tris(dimethylamino) phosphonium hexafluorophosphate (BOP) was from NEO-SYSTEMS (Strasbourg, France). N-Ethyldiisopropylamine (99%) (DIEA) was from Fluka Chemie (Neu-Ulm, Germany). Dimethyl sulfoxide (DMSO 99.9%), ovalbumin (OA), and peroxidase-labeled rabbit anti-mouse immunoglobulin ($R\alpha M^{HRP}$) were from DAKO A/S (Glostrup, Denmark). TMB-Plus substrate was from KEM-EN-TEK (Copenhagen, Denmark).

b) Materials

Microtitre plates (MaxiSorp™ and Polysorp™) were from NUNC (Roskilde, Denmark). The microtitre plate reader (Thermomax) and the analysing software: SOFTmax® PRO were from Molecular Devices (Sunnyvale, USA). Tape lids were from Avery (Nykøbing F, Denmark). The stationary dispenser was a Multidrop dispenser from Labsystems (Beverly Mass., USA). Milli-Q® equipment for water purification was from Millipore (Boston, USA).

c) Animals and immunisations

Ten to twelve weeks old female Balb/cxCF1 F1-hybrid mice were used for immunisation. One month before immunisation they were primed with 0.2 mL live BCG-vaccine intraperitonally. The antigen (25×carrier/immunogen) was absorbed onto $Al(OH)_3$ as an adjuvant. The total volume of vaccine per immunisation was 200 µL, containing 25× of antigen and 1 mL of adjuvant. The antigen was injected intraperitonally with 2-weeks intervals. Test bleedings were collected 10 days after immunisation and assayed in ELISA.

d) Monoclonal antibodies

When antibody titre's exceeded 1:2000, mice were regarded ready for fusion. The procedure as described by Köhler and Milstein (1975) was employed with minor modifications. Monoclonal antibodies were selected on basis of titre, affinity and specificity. Selected clones were recloned until monoclonality and stored frozen at −80° C.

e) Preparation of plates i) Passive adsorption: A MaxiSorp™ microtitre plate was filled by a stationary dispenser with 200 µL/well BAM-OA (16.7 ng/mL) in coating buffer. After coating over night at 4° C. the plate was washed 4 times with de-ionised water and dried 30 min at 37° C. The plate was either used immediately or sealed with tape lid and stored at room temperature in the dark until use.

ii) Covalent immobilisation:

A PolySorp™ microtitre plate was filled by a stationary dispenser with 200 µL/well BAM-OA-AQ (50 ng/mL) in 0.1×PBS. After being exposed to uv-light (300–400 nm) at 34° C. for 30 min, the plate was washed 4 times with de-ionised water and dried 30 min at 37° C. The plate was either used immediately or sealed with tape lid and stored at room temperature in the dark until use.

f) Buffers

Phosphate buffered saline (PBS): Sodium hydrogen phosphate dihydrate (28.75 g), potassium dihydrogen phosphate (5.0 g), sodium chloride (200 g) and potassium chloride (5 g) were dissolved in 24.8 L Milli-Q® water and the pH adjusted to 7.2. Phosphate buffered saline with Tween 20 (PBST): 12.5 mL Tween 20 was added to 25 L PBS.

A 10 times stronger version of this buffer (10×PBST) was used when adding the antibody to the samples to eliminate possible matrix effects. PBST was also used as washing buffer.

Coating buffer (for passive adsorption): Sodium carbonate (1.36 g) and sodium hydrogen carbonate (2.93 g) were dissolved in 900 mL Milli-Q® water followed by the addition of 2 mL saturated phenol red (0.76 mg/mL). After pH was adjusted to 9.6, Milli-Q® water was added to 1000 mL.

g) Assay method

Standards (in Milli-Q® water) and samples (150 µL) were added to the hapten-coated plate followed by the addition of 50 µL antibody (HYB 273-1) diluted in 10×PBST (66.7 ng/mL). The plate was incubated for 1 hour. After washing 4 times with PBST, the plate was incubated with 200 µL/well $R\alpha M^{HRP}$ diluted 1:1000 in PBST. After a final 6 times wash with PBST, 200 µL/well TMB-Plus was added. The colour development was stopped after 10 minutes by adding 50 µL/well 1 M $H_2SO_4$ and the absorbance was read at 450 nm.

The standards were used to generate a semi-log graph based on the 4-parameter-logistic method (Rodbard, 1974: equation 1), followed by calculation of sample values.

$$Y = \frac{(A-D)}{\left[1+\left(\frac{X}{C}\right)^B\right]} + D \qquad (1)$$

X: concentration of analyte (µg/L).

Y: absorbance at 450 nm ($A_{450}$).

A: maximum absorbance (upper asymptote).

D: minimum absorbance (lower asymptote).

C: midpoint between A and D. Extrapolation to x-axis yields the value of $IC_{50}$ (µg/L).

B: slope for the transition between A and D

These calculations were executed automatically by the software package SOFTmax® PRO Version 2.2 upon reading the microtitre plates. Measurements of the standards and the samples were based on four replicates. All incubations and colour developments were carried out with the plates wrapped in aluminium foil and placed in a closed isolating box to avoid temperature differences over the plate. During incubation, the box was mounted on an orbital shaking table (4 plate size), set to 600 rpm.

h) Water samples

Milli-Q® water and ground water were collected and spiked with different concentrations of BAM (0.05, 0.1, 0.5 and 1 $\mu$g/L). Milli-Q® water was used for preparing standards with BAM ranging from 0.0156 to 2 $\mu$g/L. The groundwater was sampled at a sandy aquifer at a depth of 6.5 meter near Vejen, Denmark and at an aquifer which mainly consisted of clay at a depth of 3 meters near Copenhagen (Ballerup), Denmark. The water from both localities was rich in organic carbon and inorganic elements due to pollution from landfills.

Example 2

Synthesis i) Typical Synthesis of a Hapten
Synthesis of EQ-0031 (hapten)

All chemicals were purchased from Aldrich Chemical Co. unless other stated. 2,4-Dichloro-3-cyano aniline: 2,6-Dichloro-3-nitro cyanobenzene (10.0 g, 46.1 mmol, Maybrigde), acetic acid (16.6 g, 276.6 mmol) and iron powder (7.7 g, 138.1 mmol) was swirled in absolute ethanol (200 mL) and refluxed over night under nitrogen. The iron powder was added in small portions to avoid dangerously violent reaction. Activated charcoal was added to the suspension and refluxed for 30 minutes. Filtration of insoluble material was carried out while the ethanol was still hot. To collect the crude product water (750 mL) was added to the ethanol. The product was obtained as a yellow solid (6.9 g, 80%) and was shown to be pure by TLC. $R_f$(petrol ether/ethyl acetate 1:1)=0.36.

N-(5-Carboxymethyl-pentyl)-2,4-dichloro-3-cyano aniline:

2,4-Dichloro-3-cyano aniline (6.0 g, 32.1 mmol), hexanoic diacid (9.5 mL, 138.3 mmol), BOP (28.4 g, 64.2 mmol, Isochem) and triethyl amine (27.0 mL, 192.6 mmol) was dissolved in 75 mL DMF. The reaction was allowed to stand for 2 days at room temperature. TLC showed an insufficient reaction and a new portion of BOP, hexanoic diacid and triethyl amine was added. The reaction was stirred for a day at room temperature. Water (750 mL) was added to the reaction. The crude mixture was extracted by dichloromethane (400 mL). The dichloromethane was extracted with sodium carbonate (10%, 3 times) and hydrochloric acid (6M, 3 times). The dichloromethane was dried with magnesium sulfate and the resulting solution was concentrated in vacuum to yield a crude oily product (6.0 g, 60%) which was used directly without further purification in the next step.

N-(5-Carboxypentyl)-2,4-dichloro-3-amido aniline:

N-(5-Carboxymethyl-pentyl)-2,4-dichloro-3-cyano aniline (2.0 g, 6.1 mmol), sodium hydroxide (25%, 1.5 mL) was dissolved in ethanol (4.0 mL). Hydrogen peroxide (30%, 2.5 mL) was added slowly to keep the temperature under 50° C. and avoid an explosion. After complete addition the reaction mixture was heated to 50° C. for 3 days. Water (20 mL) was added to the reaction and the resulting mixture was extracted with dichloromethane (3 times). The product was precipitated from the water phase by adding concentrated hydrochloric acid and then oven dried at 50° C. to yield the product as a white solid (0.75 g, 40%). The product was shown to be pure by TLC. $R_f$(ethyl acetate/acetic acid 95:5)=0.45. Melting point 179–181° C. Mass spectroscopy (MALDI-TOF): 355.0 (MNa$^+$). $^1$H-NMR (DMSO-d$_6$) $\delta$: 9.56 (s, 1H), 8.06 (s, 1H), 7.77 (s, 1H), 7.66 (d, 2H), 7.42 (d, 2H), 2.4 (t, 2H), 2.2 (t, 2H), 1.6 (m, 4H). (The acidic proton was not to be found in NMR).

ii) Synthesis of the Photo-Catalytic Coupling Moiety
Synthesis of EQ-0028 (anthraquinone)

The 6-aminohexanoic acid methylester was prepared by modification of a procedure described by Germaise et al. 1958. All final products were identified using $^1$H-NMR and mass spectroscopy. The purity of products was determined by TLC. All chemicals were purchased from Aldrich Chemical Co. unless other stated.

6-Aminohexanoic acid methylester:

6-aminohexanoic acid (20 g, 0.15 mol) was suspended in methanol (80 mL), the mixture was cooled to –20° C. (acetone/dry ice) and thionyl chloride (14 mL, 0.2 mol) was added dropwise maintaining a temperature below –10° C. After addition of all thionyl chloride the cooling bath was removed and the mixture stirred for 90 minutes at room temperature. The mixture was refluxed shortly (5 minutes) and the solvents removed in vacuum. The residue was redissolved in methanol (60 mL). The product was precipitated by addition of diethyl ether (200 mL) with cooling on an ice bath. The product was collected by filtration as a white solid (22 g, 81%). The product was shown to be pure by TLC. $R_f$(methanol)=0.13. Melting point 123–124° C. Mass spectroscopy (FAB$^+$): 146.1 (MH$^+$). $^1$H-NMR (DMSO-d$_6$) $\delta$: 8.1 (br. s, 3H), 3.60 (s, 3) 2.75 (t, 2H), 2.30 (t, 2H), 1.50 (qn, 4H), 1.30 (qn, 2H).

N-(5-carboxymethyl-pentyl)-2-anthraquinonecarboxamide:

Anthraquinone-2-carboxylic acid (2.52 g, 10 mmol) was suspended in tetrahydrofuran (THF) (100 mL). The mixture was cooled on an ice bath and dicyclohexylcarbodiimide (DCC) (2.26 g, 11 mmol, NovaBiochem) was added, followed by 3-hydroxy-1,2,3-benzotriazine-4-one (Dhbt-OH) (1.63 g, 10 mmol). The ice bath was removed and the mixture stirred overnight at room temperature. The solvent was removed in vacuum and the residue was suspended in DMF (100 ml). 6-aminohexanoic acid methylester (1.99 g, 11 mmol) was added followed by triethylamine (7 mL, 50 mmol). The mixture was stirred overnight at room temperature. DCU was removed by filtration, and the product was precipitated by addition of ice/water (200 mL). The product was collected by filtration and dried in vacuum in an exicator over sicapent. The crude was recrystallized from ethyl acetate yielding the product as yellow solid (3.1 g, 73%). The product was shown to be pure by TLC. $R_f$(ethyl acetate)=0.68. Melting point 144–145° C. Mass spectroscopy (FAB$^+$): 380.1 (MH$^+$). $^1$H-NMR (DMSO-d$_6$) $\delta$: 9.00 (t, 1H), 8.75 (s, 1H), 8.40 (dd, 1H), 8.30 (m, 3H), 8.05 (m, 2H), 3.70 (s, 3H), 3.40 (q, 2H) 2.40 (t, 2H), 1.70 (qn, 4H), 1.40 (qn, 2H).

N-(5-carboxypentyl)-2-antraquinonecarboxamide:

N-(5-carboxymethyl-pentyl)-2-anthraquinonecarboxamide (0.95 g, 2.5 mmol) was suspended in THS (15 mL) and aqueous lithium hydroxide (15 mL, 0.5M) was added, the mixture was stirred for 2 hours at room temperature. THF was evaporated in vacuum and the product precipitated by addition of aqueous HCl (6 mL, 2M). The product was collected by filtration and dried in vacuum to give the product as a yellow solid (0.822 g, 90%). The product was shown to be pure by TLC. $R_f$(petrolether/ethyl acetate/acetic acid 50:50:5)=0.43. Melting point 198–199° C. Mass spectroscopy (FAB$^+$): 366.2 (MH$^+$). $^1$H-NMR (DMSO-d$_6$) δ: 12.00 (br. s, 1H), 9.00 (t, 1H), 8.75 (s, 1H), 8.40 (dd, 1H), 8.35 (m, 3H), 8.0 (m, 2H), 2.30 (t, 2H), 1.60 (qn, 4H), 1.40 (qn, 2H).

Example 3

Preparation of Comjugates for Immobilisation a) Conjugation of BAM-hapten (EQ-0031) and anthraquinone (EQ-0028) to ovalbumin Ovalbumin (OA) was conjugated with a BAM hapten (EQ-0031, FIG. 1B) to form a hapten-OA conjugate and a portion was used for passive adsorption (FIG. 28). Another portion of this conjugate was subsequently conjugated with an anthraquinone (AQ), (EQ-0028, FIG. 1C) and used for covalent immobilisation (FIG. 2A).

The conjugations required a preliminary activation. EQ-0031 (BAM hapten) or EQ-0028 (AQ) (35.3 μmol) and BOP (35.3 μmol) were dissolved in 1.5 mL dry DMSO followed by the addition of 18.5 μL DIEA (105.9 μmol). After approximately 10 min, the hapten was ready for polymer carrier conjugation. One μL of this hapten solution corresponds to one mole equivalent of 1 mL of 1 mg/mL ovalbumin. EQ-0031 was added as 5 mole equivalents (5 μL) to 1 mL of a 1 mg/mL protein in 0.1 M sodium hydrogen carbonate pH 8.1. The tube was agitated for 2 hours in the dark at room temperature and stored overnight at 4° C. before use to complete the conjugation. For covalent immobilisation, the BAM-OA conjugate was subsequently conjugated with 10 mole equivalents (10 μL) EQ-0028, following the same procedure as for EQ-0031. Finally, the BAM-OA-AQ (FIG. 2A) conjugate was dialysed against PBS and verified spectrophotometrically.

Example 4

Results: Comparison of Passive Adsorption and Covalent Immobilisation

To compare the performances of the two ELISA methods with antigen coated by passive adsorption to that by covalent immobilisation respectively, standard curves were generated with BAM standards ranging from 0.0156 to 2 μg/L on each surface using the identical assay procedures. The data were normalised by the % B/B$_0$ transformation (eq 2). The normalised data were then plotted vs. BAM concentration and the four-parameter-logistic equation (eq 1) was fitted to the experimental points (FIG. 3).

In this circumstance, the covalent immobilisation technique performed better than conventional passive adsorption. In another circumstance, where another antigen, antibody, or polymer carrier-spacer had been used, the performance of both techniques would have differed to the extent where their respective performances were identical or favoured passive adsorption.

Performance was measured by coefficients of variations (CV). The coefficient of variation is a reflection of the reliability of an assay. The CV of the photocoupled covalent immobilisation technique shown in FIG. 3A was 3.36% whereas the CV for the passive adsorption technique shown in FIG. 3B was 15.20%. CVs were determined from standard curves. The standard curves were plotted by quadruple determinations of the mean reading at a particular analyte concentration over repeated assays over a range of concentrations. FIG. 3 shows the variations of normalised readings of quadruple determinations for the standard curves for the plates which were covalently immobilised as compared to the plates in which passive adsorption was the means of adsorbing hapten.

Example 5

Results: Detection Limits and Sensitivity

As to detection limits (defined as the analyte concentration giving a 15% decrease in maximum signal: DL$_{15}$) and sensitivity (defined as the analyte concentration giving a 50% decrease in maximum signal: IC$_{50}$) the two surface performs almost equally. However, considering the variance coefficients of the quadruplicate determinations, the covalent immobilisation clearly showed the best performance. Further development of the BAM assay was therefore based on this technology and the following results are generated on PolySorp™ microtire plates covalently coated with BAM-OA-AQ as described herein in the Preparation of plates section As shown in FIG. 3A, the DL$_{15}$ for this assay on the photo catalysed covalent immobilisation was calculated to 0.02 μg/L of BAM and the IC$_{50}$ to 0.19 μg/L of BAM. This range was subject to verification by recovery studies presented in Table 2.

As shown in FIG. 3B, the DL$_{15}$ for this assay on surfaces immobilised by passive adsorption calculated to 0.045 μg/L of BAM and the IC$_{50}$ to 0.14 μg/L of BAM. This range was subject to verification by recovery studies presented in Table 2.

Example 6

Results: Specificity

To evaluate the specificity of the assay, several analytes with BAM-related structures (Table 3) were assayed in concentrations up to 100 mg/L. The cross-reactivities were calculated for each analyte by comparing the IC$_{50}$ value of the analyte with the IC$_{50}$ value of BAM according to equation 3. As it can be seen, this assay is very specific for BAM with the highest cross-reactivity to 2,4-dichlorobenzamide at 3.8 percentage. It is noteworthy that there is no measurable cross-reactivity to Dichlorbenil, which is the parent-compound to BAM (FIG. 1A).

Example 7

Results: Matrix Effects and Recovery

Both inter-assay accuracy, precision and matrix effects were evaluated by a recovery study using three different types of water spiked with BAM (Table 2). The samples were spiked with 0.05, 0.1, 0.5 and 1 μg/L BAM and then analysed 4 times over 4 days. The recovery data show that the assay performs reliable in the investigated range (0.5 to 1 μg/L BAM) with an average recovery of 104.1 percent. The samples without BAM were, however, estimated to contain up to 0.021 μg/L BAM unveiling a slight risk for false positives. The average inter-assay CV for the spiked samples was 4:3 percent. Table 2 also indicates there were no significant matrix effects for the two ground water types as compared to Milli-Q® water. This is corroborated by Table 1, which indicateds the Dissolved Organic Carbon (DOC) content in each of the samples and standards, and shows that elevated levels of DOC, which is common in many samples, does not disturb the assay.

Example 8

Results: Comparative Analysis of Method

Samples were analysed using the method described herein and results compared to results obtained form the same samples using the current method of analysis for BAM in ground water. The assay method was performed as described in the subheading Assay Method (Example 1g). The plates were prepared in the usual fashion using covalent immobilisation by means, in this instance, of photocatalytic immobilisation using the anthraquinone to link the polymer carrier (EQ-0028). Ovalbumin as the polymer carrier, and EQ-0031 as the hapten (see FIG. 2A).

Preparation of BAM-plates

A PolySorp™ microtire plate was filled by a stationary dispenser with 200 μL/well EQ0031-OA-EQ0028 (50 ng/mL) in 0.1×PBS. After being exposed to UV-light (300–400 nm) at 34° C. for 30 min, the plate was washed 4 times with de-ionised water and dried 30 min at 37° C. The plate was either used immediately or sealed with tape lid and stored at room temperature in the dark unit use.

GC-MS

The water sample (500 mL) is acidified to pH=3 and internal standards are added corresponding to 0.05 μg/L followed by the addition of 20 g NaCl. The sample is then extracted by 30+10+10 mL dichloromethane. The extracts are evaporated to a final volume of 200 μL The sample was analysed by GC-MS applying selective ion monitoring (SIM).

| Column | Sil 13 CB Fused silica Capillary Column 50 m × 0.32 mm × 1.2 μm |
|---|---|
| Carrier gas | Helium |
| Pressure | 10 Psi |
| Injection | 1 μL, splitless |
| Injector temperature | 250° C. |
| Column temperature | 85° C. (2 min.). 10° C./min. until 280° C. (3 min.) |

Linear Regression

The dotted line of FIG. 5 represents a calculated linear regression to the points on the graph. The equation for a straight line is Y=a+b(X). a is the point of interception on the vertical axis (Y) and b is the slope parameter for the line. X is the horizontal axis. The equation for the solid line will be Y=0+1(X).

$R^2$ is the coefficient of correlation. A perfect regression to the data points will have a $r^2=1$. Comparative analysis results indicate an $R^2$ value of 0.9323, clearly indicating that the methods are comparable and thus that the immunoassay is equally accurate to GC-MS. These parameters were all calculated by the software package "SigmaPlot 5.0".

Example 9

Results: Shelf-Life of Plates

FIG. 4 shows how the performance of the stored plates (black symbols) was affected during the time of storage. As it can be seen neither maximum signal, $IC_{50}$ nor CV was significantly changed during time as compared to freshly prepared plates (white symbols).

What is claimed is:

1. An immunogenic hapten-carrier complex comprising an immunogenic carrier and a compound of the following formula 1:

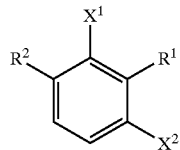

wherein $R^2$ is a linking unit to the carrier to form the hapten-carrier complex;

$R^1$ is selected from the group consisting of —C(=O)—N($R^5$)($R^5$), —N($R^5$)—C(=O)—$OR^5$, —C(=O)—$OR^5$, —N($R^5$)—C(=O)($R^5$), —N($R^5$)—C(=S)($R^5$), —C(=S)—N($R^5$)($R^5$), —N($R^5$)—C(=S)—N($R^5$)($R^5$),—N($R^5$)—C(=O)—N($R^5$)($R^5$), —O—C(=O)—$R^5$, —C(=S)—$OR^5$, —O—C(=S)—$R^5$, —$O^5R^5$, —N($R^5$)($R^5$), —S—$R^5$, —$CH_3$—$R^5$, —CN, and halogen;

each $R^5$ is independently selected from the group consisting of hydrogen, optionally substituted $C_{1-4}$ alkyl, optionally substituted $C_{2-5}$ alkenyl, optionally substituted $C_{2-8}$ alkynyl, optionally substituted aryl, optionally substituted heteroaryl, and optionally substituted $C_3$–$C_7$ cycloalkyl; and $X^1$ and $X^2$ are the same or different and are each a halogen.

2. A complex of claim 1 wherein $R^2$ is selected from the group consisting of —C(=O)—N($R^5$)—$(CH_2)_n$—$R^3$—$(CH_2)_m$—$R^4$, —N($R^5$)—C(=O)—$(CH_2)_n$—$R^3$—$(CH_2)_m$—$R^4$, —O$(CH_2)_m$—$R^3$—$(CH_2)_m$—$R^4$, —N($R^5$)—$(CH_2)_m$—$R^3$—$(CH_2)_m$—$R^4$, —S—$(CH_2)_n$$R^3$—$(CH_2)_m$$R^4$—$(CH_2)_n$—$R^4$,—$(CH_2)_m R^4$, —C(=O)—O—$(CH_2)_n$—$R^3$—$(CH_2)_m$—$R^4$ and —O—C(=O)—$(CH_2)_n$—$R^3$—$(CH_2)_m$—$R^4$ n and m are the same or different integers from 0 to 8;

$R^3$ is selected from the group consisting of —O—C(=O)—, —C(=O)—O—, —O—C(=S)—, —C(=S)—O—, —N($R^5$)—C(=O)—, —C(=O)—N($R^5$)—, —O—, —S—, —N($R^5$)—, optionally substituted $C_{4-t}$, allelete, optionally substituted arylene, optionally substituted heteroarylene, an optionally substituted $C_3$–$C_7$ cycloalkylene, $R^4$ is selected from group consisting of an activated form of a carboxyl, carboxylic acid, amine, acyl halides, activated esters, thiols, disulphides (—S—S—R), halides, sulphonates, quinones and imides; and $R^5$ is hydrogen, optionally substituted $C_{1-4}$ alkyl, optionally substituted $C_{2-5}$ alkenyl, optionally substituted $C_{2-5}$ alkenyl, optionally substituted $C_{2-8}$ alkynyl, optionally substituted aryl, optionally substituted heteroaryl, and optionally substituted $C_3$–$C_7$ cycloalkyl.

3. A complex of claim 1 wherein $R^2$ is selected from the group consisting of —C(=O)—N($R^5$)—$(CH_2)_n$—$R^3$—$(CH_2)_m$—$R^4$, —N($R^5$)—C(=O)—$(CH_2)_n$—$R^3$—$(CH_2)_m$—$R^4$, O—$(CH_2)_m$—$R^3$ $(CH_2)_m$—$R^4$, —O—C(=O)—$(CH_2)_m$—$R^3$—$(CH_2)_m$—$R^4$ and —O—C(=O)—$(CH_2)_n R^3$—$(CH_2)_m$—$R^4$.

4. A complex of claims 2 or 3 wherein the sum of m and n is between 0 to 8.

5. A complex of claims 2 or 3 wherein $^3$ is selected from the group consisting of —O—C(=O)—, —C(=O)—O—, —N($R^5$)—C(=O)—O, —O—C(=O)—N($R^5$)—, —O—, —N($R^5$)—, optionally substituted $C_{1-4}$, alkylene, optionally substituted arylene, optionally substituted heteroarylene and optionally substituted $C_{3-7}$ cycloalkylene.

6. A complex of claim 2 or 3 wherein $R^3$ is selected from the group consisting of optionally substituted $C_{1-4}$, alkylene, optionally substituted arylene, optionally substituted heteroarylene and an optionally substituted $C_{3-7}$ cycloalkylene.

7. A complex of claim 6 wherein $R^3$ is selected from the group consisting of optionally substituted $C_{1-4}$, alkylene, optionally substituted arylene, optionally substituted $C_{3-7}$ cycloalkylene.

8. A complex of claim 7 wherein $R^3$ is selected from the group consisting of optionally substituted $C_{1-4}$, alkylene and optionally substituted $C_{3-7}$ cycloalkylene.

9. A complex of claim 7 wherein $R^3$ is selected from the group consisting of optionally substituted $C_{1-4}$, alkylene.

10. A complex of claim 3 wherein $R^2$ is —NH—C(=O)—(CH$_2$)$_4$—R$^4$.

11. A complex of claim 10 wherein $R^2$ is —NH—C(=O)—(CH$_2$)$_4$—COOH.

12. A complex of claim 64 wherein $R^1$ is selected from the group consisting of —C(=O)—N(R$^5$)(R$^5$), —N(R$^5$)—C(=O)—OR$^5$, —C(=O)—OR$^5$, —N(R$^5$)—C(=O)—(R$^5$), —C(=S)(R$^5$), —C(=S)(R$^5$), —(=S)—N(R$^5$)(R$^5$), —N(R$^5$)—C(=S)—N(R$^5$)(R$^5$), —N(R$^5$)—C(=O)—N(R$^5$)(R$^5$), —N(R$^5$)(R$^5$), and —CN.

13. A complex of claim 12 wherein $R^1$ is selected from the —C(=O)—N(R$^5$)(R$^5$), —C(=S)N(R$^5$)(R$^5$), —N(R$^5$)—C(=O)—OR$^5$, —N(R$^5$)—C(=O)(R$^5$) and —CN.

14. A complex of claim 13 wherein $R^1$ is —C(=O)—N(R$^5$)(R$^5$).

15. A complex of claim 13 wherein $R^1$ is —C(=O)—NH$_2$.

16. A complex of any one of claims 1 through 3 wherein $R^4$ is selected from the group consisting of carboxylic acid, acid anhydride, activated ester of a carboxylic acid and a carbodiimide of a carboxylic acid.

17. A complex of claim 16 wherein $R^4$ is selected from the group consisting of carboxylic acid and a carbodiimide.

18. A complex of any one of claims 1 through 3 wherein each $R^5$ is independently selected from the group consisting of hydrogen, optionally substituted $C_{1-4}$ alkyl, optionally substituted $C_{2-5}$ alkenyl, optionally substituted $C_{2-8}$ alkynyl, optionally substituted aryl, and optionally substituted $C_3$–$C_7$ cycloalkyl.

19. A complex of claim 18 wherein $R^4$ is independently selected from the group consisting of hydrogen, optionally substituted $C_{1-4}$ alkyl, optionally substituted $C_{2-5}$ alkenyl, optionally substituted $C_{2-5}$ alkynyl, and optionally substituted $C_{3-7}$ cycloalkyl.

20. A complex of claim 19 wherein $R^5$ is independently selected from the group consisting of hydrogen, optionally substituted $C_{1-4}$ alkyl, optionally and optionally substituted $C_3$–$C_7$ cycloalkyl.

21. A complex of claim 20 wherein $R^5$ is independently selected from the group consisting of hydrogen and optionally substituted $C_{1-4}$ alkyl.

22. A complex according to claim 20 wherein $R^5$ is hydrogen.

23. A complex of claim 20 wherein $X^1$ is chlorine.

24. A complex of claim 1 wherein $X^2$ is chlorine.

25. A complex of claim 1 wherein the carrier is a polymer.

26. A complex of claim 1 wherein the carrier is a protein.

27. A complex of claim 1 wherein the carrier comprises the protein ovalbumin.

28. A complex of claim 1 wherein $R^2$ is linked to the protein ovalbumin.

29. An assay comprising contacting a test sample with antibodies obtainable from the complex of claim 1, and detecting bindnig of the antiody to a 1,3-dihalo aromatic pesticide in the sample, wherein binding indicates the presence of the 1,3-dihalo aromatic pesticide in the sample.

30. The assay of claim 29 wherein one or more 1,3-dihalo aromatic pesticides in the test sample are quantitatively detected.

31. The assay of claim 30 wherein the 1,3-dihalo aromatic pesticide is selected from the group consisting of dichlorobenil, chlorthiamid, and their derivatives and degradation products.

32. The assay of any one of claims 29 and 30 wherein the assay further comprises:
(a) providing a complex comprising a compound of the following formula II immobilized to solid support,

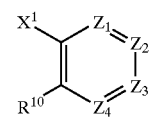

II wherein $X^1$ is a halogen;
$Z_1$ is C—R$^6$, $Z_2$ is C—R$^7$ $Z_3$ is C—R$^6$ and $Z_4$ is C—R$^9$, where at least one of R$^6$—R$^{10}$ is present and serves as a linking unit for immobilization of the hapten to the solid support, and those of R$^6$–R$^{10}$ which are present and which do serve as a linking unit are independently selected from the group consisting of —C(=O)—NH$_2$, —N(R$^5$)(R$^5$), —CN, —N(R$^5$)—C(=O)(R$^5$), —N(R$^5$)—C($^-$S)(R$^5$), —C(=S)—N(R$^5$)(R$^5$), —N(R$^5$)—C(=S)—N(R$^5$)(R$^5$), —N(R$^5$)—C(=O)—N(R$^5$)(R$^5$), —N(R$^5$)—C(=O)—OR$^5$, —(R$^5$), —C(=O)—N(R$^5$)(R$^5$),—C(=O)—OR$^5$, —C(=S)—OR$^5$, —O—C(=S)—R$^5$, hydrogen, and halogen;
wherein those of R$^6$—R—$^{10}$ which serve as a linking unit are selected from the group consisting of —C(=O)—N(R$^5$)—(CH$_2$)$_n$—R$^3$—(CH$_2$)$_m$—R$^4$, —N(R$^5$)—C(=O)—(CH$_2$)$_n$—R$^3$—(CH$_2$)$_m$—R$^4$, —O—(CH$_2$)$_n$R$^3$—(CH$_2$)$_m$—R$^4$, —N(R$^5$)—(CH$_2$)$_n$—R$^3$—(CH$_2$)$_m$—R$^4$, —S—(CH$_2$)$_n$—R$^3$—(CH$_2$)$_m$—R$^4$, —(CH$_2$)$_{n+1}$—R$^{3-}$(CH$_2$)$_m$—R$^4$—C(=O)—O—(CH$_2$)$_n$—R$^3$—(CH$_2$)$_m$—R$^4$, and —O—C(=O)—(CH$_2$)$_n$—R$^3$—(CH$_2$)$_m$—R$^4$; wherein n and m are the same or different and are integers from 0 to 8;
$R^3$ is selected from the group consisting of —O—C(=O)—, —C(=O)—O—, —O—C(=S)—, —C(=S)—O—, —N)R$^5$)—C(=O)—, —C(=O)—N(R$^5$)—, —O—, —S—, —N(R$^5$)—, optionally substituted $C_{1-4}$ alkylene, optionally substituted arylene, optionally substituted heteroarylene, an optionally substituted $C_3$–$C_7$ cycloalkylene;
$R^4$ is selected from group consisting of activated forms of carboxyl, carboxylic acid, amine, acyl halides, activated esters, thiols, disuplhides, halides, sulphonates, quinones and imides; and
$R^5$ is independently selected from the group consisting of hydrogen, optionally substituted $C_{1-4}$ alkyl, optionally substituted $C_{2-5}$ alkenyl, optionally substituted $C_{2-8}$ alkynyl, optionally substituted aryl, optionally substituted heteroaryl, and optionally substituted $C_3$–$C_7$ cycloalkyl; and
(b) contacting the test sample, with the complex.

33. The assay of claim 32 wherein those of R$^6$–R$^{10}$ which serve as a linking unit are selected from a group consisting of —C(=O)—N(R$^5$)—(CH2)$_n$—R$^3$—(CH2)$_m$—R$^4$ and —N(R)—C(=O)—(CH2), —R$^3$—(CH2)$_m$—R$^4$.

34. The assay of claim 32 wherein no more than 1 of R$^6$–R$^{10}$ is a halogen.

35. The assay of claim 32 wherein no more than 2 of $R^6$–$R^{10}$ is a hydrogen.

36. The assay of claim 32 wherein no more than one member of $R^6$–$R^{10}$ serves as a linking unit.

37. The assay of claim 32 wherein the immobilizatoin is based on covalent immobilization to the solid support.

38. The assay of claim 37 wherein providing the covalent immobilizatoin comprises photocatalysis.

39. The assay of claim 32 wherein the immobilization is based on passive adsorption to the solid support.

40. A method for identification or quantification of a 1,3-dihalo aromatic pesticide or one or more degradation products thereof, comprising:
(a) contacting a test sample with antibodies obtainable from a hapten-carrier complex comprising an immunogenic carrier and a compound of the following formula 1:

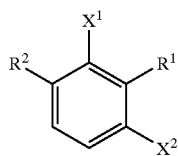

I wherein $R^2$ is a linking unit to the carrier to form the hapten-carrier complex;

$R^1$ is selected from the group consisting of —C(=O)—N($R^5$)($R^5$), —N($R^5$)—C(=O)—O$R^5$, —C(=O)—O$R^5$, —N($R^5$)—C(=O)($R^5$), —N($R^5$)—C(=S)($R^5$), —C(=S)—N($R^5$)($R^5$), —N($R^5$)—C(=S)—N($R^5$)($R^5$), —N($R^5$)—C(=O)—N($R^5$)($R^5$), —O—C(=O)—$R^5$, —C(=S)—O$R^5$, —O—C(=S)—$R^5$, —O$^5R^5$, —N($R^5$)($R^5$), —S—$R^5$, —CH$_2$—$R^5$, —CN, and halogen;

each $R^5$ is independently selected from the group consisting of hydrogen, optinally substituted $C_{1-4}$ alkyl, optinally substituted $C_{2-5}$ alkenyl, optionally substituted $C_{2-8}$ aklynyl, optionally substituted aryl, optionally substituted heteroaryl, and optionally substituted $C_3$–$C_7$ cycloalky; and $X^1$ and $X^2$ are same or different and are each a halogen, and a compound of the following formula II immobilized to a solid support,

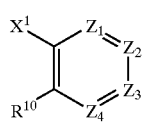

II wherein $X^1$ is a halogen;

$Z_1$ is C—$R^6$, $Z_2$ is C—$R^7$ $Z_3$ is C—$R^8$ and $Z_4$ and is C—$R^9$, where at least one of $R^6$–$R^{10}$ is present and serves as a linking unit for immobilization of the hapten to the solid support, and those of $R^{6[8]}$–$R^{10}$ which are present and which do not serve as a linking unit are independently selected from the group consisting of —C(=O)—NH$_2$, —N($R^5$)($R^5$), —CN, —N($R^5$)—C(=O)($R^5$), —N($R^5$)—N($R^5$)—C(⁻S)($R^5$), —C(=S)—N($R^5$)($R^5$), —N($R^5$)—C(=S)—N($R^5$)($R^5$), —N($R^5$)—C(=O)—N($R^5$)($R^5$), —N($R^5$)—C(=O)—O$R^5$, —C(=O)—N($R^5$)($R^5$), —C(=O)—O$R^5$, —C(=S)—O$R^5$, —O—C(=S)—$R^5$, hydrogen, and halogen;

wherein those of $R^6$–$R^{10}$ which serve as a linking unit are selected from the group consisting of —C(=O)—N($R^5$)—(CH$_2$)$_n$—$R^3$—(CH$_2$)$_m$—$R^4$, —N($R^5$)—C(≦O)—(CH$_2$)$_n$$R^3$—(CH$_2$)$_m$—$R^4$, —O—(CH$_2$)$_n$$R^3$—CH$_2$)$_m$—$R^4$, —N($R^5$)—(CH$_2$)$_n$—$R^3$—CH$_2$)$_m$—$R^4$, —S—(CH$_2$)$_n$—$R^3$—(CH$_2$)$_m$—$R^4$, (CH$_2$)$_{n+1}$—$R^3$—(CH$_2$)$_m$—$R^4$, —C(=O)—O—(CH$_2$)$_n$—$R^3$—(CH$_2$)$_m$—$R^4$, and —O—C(=O)—(CH$_2$)$_n$—$R^3$—(CH$_2$)$_m$—$R^4$;wherein n and m are the same or different and are integers from 0 to 8;

$R^3$ is selected from the group consisting of —O—C(=O)—, —C(=O)—O—, —O—C(=S)—, —C(=S)—O—, —N($R^5$)—C(=O)—, —C(=O)—N($R^5$)—, —O—, —S—, —N($R^5$)—, optionally substituted $C_{1-4}$ alkylene, optionally substituted arylene, optionally substituted heteroarylene, and optionally substituted $C_3$–$C_7$ cycloalkylene;

$R^4$ is selected from the group consisting of activated forms of carboxyl, carboxylic acid, amine, acyl halides, activated esters, thiols, disulphides, halides, sulphonates, quinones and imides; and $R^5$ is independently selected from the group consisting of hydrogen, optionally substituted $C_{1-4}$ alkyl, optionally substituted $C_{2-5}$ alkenyl, optionally substituted $C_{2-5}$ alkynyl, optionally substituted aryl, optionally substituted heteroaryl, and optionally substituted $C_3$–$C_7$ cycloalkyl; and (b) detecting binding of the antibody to the pesticide, wherein binding indicates the presence of the 1,3-dihalo aromatic pesticide in the sample.

41. The method of claim 40, wherein a 1,3-dihalo aromatic pesticide in the test sample is quantitatively detected.

42. The method of claim 40 or 41 the pesticide is selected from the group consisting of dichlorobenil, chlorthiamid, and derivatives and degradable products thereof.

43. The method of claim 40 or 41 wherein the pesticide is selected from the group consisting of 2,6-dichlorobenzamide, 3-hydroxy-2,6-dichlorobenzamide and sugar conjugates thereof and 4-hydroxy-2,6-dichlorobenzamide and sugar conjugates thereof.

44. The method of claim 40 or 41 the pesticide is selected from the group consisting of 2,6-dichlorobenzamide, 3-hydroxy-2,6-dichlorobenzamide and 4-hydroxy-2,6-dichlorobenzamide.

45. A method according to claim 40 or 41 wherein the pesticide is 2,6-dichlorobenzamide.

46. A method according to claim 40 wherein the compound immobilized on the solid support has a structure corresponding to formula I.

47. A method according to claim 40 wherein the compound immobilized on the solid support and the component from which the antibodies are obtainable are the same compound.

48. A method according to claim 40 wherein the DL15 is 0.1 g/L or less.

49. A method according to claim 40 wherein the DL25 is 0.05 g/L or less.

50. A method according to claim 40 wherein the IC50 is 0.5 g/L or less.

51. A method according to claim 40 wherein the IC50 is 0.3 g/L or less.

52. A method according to claim 40 wherein the coefficient of variation is less than 20%.

53. A method according to claim 40 wherein the asay is heterogeneous.

54. A method according to claim 40 wherein the solid support is selected from the group of consisting of organic polymers, glasses and/or ceramics, silicium and silicium oxide and composite materials thereof.

55. A method according to claim 40 wherein the solid support is comprised of an organic polymer selected from the group consisting of polystyrene, polycarbonate, polypropylene, polyethylene, cellulose, nitrocellulose, agarose, polyethyleneglycol terephthalate, polyvinylacetate, polyvinyldifluoride, polymethylpentene, polyvinylpyrrolidinone, polyacrylate, polyacrylonitrile, polymethylmethacrylate and polyvinylchloride, particularly polystyrene and polycarbonate.

56. A method according to claim 40 wherein the solid support is glass and/or ceramic selected from the group consisting of borosilicate glass and soda-lime glass and wherein said soda-lime glass is in a form selected from the group consisting of a specimen tube, vial, and slide for microscopy.

57. A method according to any of claims 40, 55 or 56 wherein the body of the solid support is in a form of a sheet, a film, a bead, a pellet, a disc, a plate, a ring, a rod, a net, a membrane, a filter, a tray, a microplate, a stick, a slide, or a tube.

58. A method according to claim 40 wherein the solid support comprises agarose, cellulose, polystyrene beads or a polystyrene microtire plate.

59. A method according to claim 40 wherein the solid support comprise a polystyrene microtire plate.

60. A method according to claim 59 wherein providing the covalent immobilization comprises photocatalysis.

61. A method according to claim 60 wherein providing the covalent immobilization comprises photocatalysis.

62. A method according to claim 40 wherein the immobilization is based on passive adsorption to the solid support.

* * * * *